(12) United States Patent (10) Patent No.: US 9,180,166 B2
Arinzeh et al. (45) Date of Patent: *Nov. 10, 2015

(54) CARTILAGE REPAIR SYSTEMS AND APPLICATIONS UTILIZING A GLYCOSAMINOGLYCAN MIMIC

(75) Inventors: Treena Arinzeh, West Orange, NJ (US); George Collins, Maplewood, NJ (US); Piyush Modak, Harrison, NJ (US); Ling-Fang Tseng, Syracuse, NY (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/097,657

(22) Filed: Apr. 29, 2011

(65) Prior Publication Data

US 2011/0274742 A1 Nov. 10, 2011

Related U.S. Application Data

(63) Continuation-in-part of application No. 12/661,242, filed on Mar. 12, 2010.

(60) Provisional application No. 61/329,172, filed on Apr. 29, 2010.

(51) Int. Cl.
| | | |
|---|---|---|
| *A61F 13/00* | (2006.01) | |
| *C12N 5/00* | (2006.01) | |
| *C12N 5/02* | (2006.01) | |
| *A61K 38/18* | (2006.01) | |
| *A61L 27/26* | (2006.01) | |
| *A61L 27/38* | (2006.01) | |
| *A61L 27/52* | (2006.01) | |
| *C08L 1/02* | (2006.01) | |
| *C08L 1/16* | (2006.01) | |
| *C08L 5/08* | (2006.01) | |
| *C12N 5/077* | (2010.01) | |
| *D01D 5/00* | (2006.01) | |
| *D01F 2/24* | (2006.01) | |
| *D01F 9/00* | (2006.01) | |
| *A61K 47/38* | (2006.01) | |
| *A61K 35/28* | (2015.01) | |
| *A61K 9/00* | (2006.01) | |
| *A61K 9/06* | (2006.01) | |

(52) U.S. Cl.
CPC ............ *A61K 38/1841* (2013.01); *A61K 9/0024* (2013.01); *A61K 9/06* (2013.01); *A61K 35/28* (2013.01); *A61K 47/38* (2013.01); *A61L 27/26* (2013.01); *A61L 27/3834* (2013.01); *A61L 27/52* (2013.01); *C08L 1/02* (2013.01); *C08L 1/16* (2013.01); *C08L 5/08* (2013.01); *C12N 5/0655* (2013.01); *D01D 5/0007* (2013.01); *D01F 2/24* (2013.01); *D01F 9/00* (2013.01); *A61L 2430/06* (2013.01); *C12N 2533/72* (2013.01); *C12N 2533/78* (2013.01)

(58) Field of Classification Search
None
See application file for complete search history.

(56) References Cited

U.S. PATENT DOCUMENTS

| | | |
|---|---|---|
| 4,846,835 A | 7/1989 | Grande |
| 5,030,225 A | 7/1991 | Aebischer et al. |
| 5,250,843 A | 10/1993 | Eichelberger |
| 5,353,498 A | 10/1994 | Eillion |
| 5,486,359 A | 1/1996 | Caplan |
| 5,522,879 A | 6/1996 | Scopelianos |
| 5,626,861 A | 5/1997 | Laurencin et al. |
| 5,666,467 A | 9/1997 | Colak |
| 5,681,873 A | 10/1997 | Norton et al. |
| 5,766,618 A | 6/1998 | Laurencin et al. |
| 5,811,094 A | 9/1998 | Caplan |
| 5,827,735 A | 10/1998 | Young |
| 5,841,193 A | 11/1998 | Eichelberger |
| 5,906,934 A | 5/1999 | Grande et al. |
| 5,955,529 A | 9/1999 | Imai et al. |
| 6,095,148 A | 8/2000 | Shastri et al. |
| 6,165,486 A | 12/2000 | Marra et al. |
| 6,174,333 B1 | 1/2001 | Kadiyala |
| 6,214,369 B1 | 4/2001 | Grande et al. |
| 6,306,424 B1 | 10/2001 | Vyakarnam |
| 6,355,239 B1 | 3/2002 | Bruder |
| 6,387,367 B1 | 5/2002 | David-Sproul |
| 6,464,983 B1 | 10/2002 | Grotendorst |
| 6,472,210 B1 | 10/2002 | Holy et al. |
| 6,482,231 B1 | 11/2002 | Abatangelo |

(Continued)

FOREIGN PATENT DOCUMENTS

| | | |
|---|---|---|
| WO | PCT/US2005/043876 | 12/2005 |
| WO | WO 2006/068809 | 6/2006 |
| WO | WO 2006095021 A1 * | 9/2006 |
| WO | WO 2008055038 A2 * | 5/2008 |
| WO | PCT/US2008/067322 | 6/2008 |
| WO | PCT/US2012/050156 | 8/2012 |

OTHER PUBLICATIONS

Nettles et al, "Potential Use of Chitosan as a Cell Scaffold Material for Cartilage Tissue Engineering," Tissue Engineering, vol. 8, No. 6, pp. 1009-1016 (2002).*

Sittinger et al, "Current Strategies for Cell Delivery in Cartilage and Bone Regeneration," Current Opinion in Biotechnology, vol. 15, Issue 5, pp. 411-418 (2004).*

Endres et al, "Osteogenic Induction of Human Bone Marrow-Derived Mesenchymal Progenitor Cells in Novel Synthetic Polymer-Hydrogel Matrices," Tissue Engineering, vol. 9, No. 4, pp. 689-702 (2003).*

(Continued)

*Primary Examiner* — Dennis J Parad
(74) *Attorney, Agent, or Firm* — McCarter & English, LLP

(57) ABSTRACT

The present invention relates to hydrogel or scaffold compositions and methods of use for cell growth and/or regenerative medicine. The hydrogel comprises a water soluble cellulose compound and, in certain aspects, a fibrous or filamentous matrix. The hydrogels as described provide a support or scaffold that promotes, facilitates, and/or enhances progenitor or stem cell growth and/or differentiation. In addition, the hydrogel is useful for tissue, e.g., cartilage, regeneration and repair.

30 Claims, 6 Drawing Sheets

(56) References Cited

U.S. PATENT DOCUMENTS

| | | | |
|---|---|---|---|
| 6,489,165 | B2 | 12/2002 | Bhatnagar et al. |
| 6,511,511 | B1 | 1/2003 | Slivka et al. |
| 6,541,024 | B1 | 4/2003 | Kadiyala |
| 6,685,956 | B2 | 2/2004 | Chu |
| 6,689,166 | B2 | 2/2004 | Laurencin |
| 6,689,374 | B2 | 2/2004 | Chu et al. |
| 6,730,252 | B1 | 5/2004 | Teoh et al. |
| 6,783,712 | B2 | 8/2004 | Slivka et al. |
| 6,790,455 | B2 | 9/2004 | Chu |
| 6,790,528 | B2 | 9/2004 | Wendorff |
| 6,863,900 | B2 | 3/2005 | Kadiyala |
| 7,012,106 | B2 | 3/2006 | Yuan et al. |
| 7,022,522 | B2 | 4/2006 | Guan et al. |
| 7,247,313 | B2 | 7/2007 | Roorda et al. |
| 7,271,234 | B2 | 9/2007 | Kohn et al. |
| 7,601,525 | B2 | 10/2009 | Batich et al. |
| 7,619,901 | B2 | 11/2009 | Eichelberger et al. |
| 7,767,221 | B2 | 8/2010 | Lu et al. |
| 7,803,574 | B2 | 9/2010 | Desai |
| 2002/0004039 | A1 | 1/2002 | Reid et al. |
| 2002/0034796 | A1 | 3/2002 | Shastri et al. |
| 2002/0173213 | A1 | 11/2002 | Chu et al. |
| 2003/0054035 | A1 | 3/2003 | Chu et al. |
| 2003/0069369 | A1 | 4/2003 | Belenkaya et al. |
| 2003/0077311 | A1 | 4/2003 | Vyakarnam et al. |
| 2003/0211130 | A1 | 11/2003 | Sanders et al. |
| 2004/0018226 | A1 | 1/2004 | Wnek |
| 2005/0095695 | A1 | 5/2005 | Shindler et al. |
| 2005/0196423 | A1 | 9/2005 | Batich et al. |
| 2006/0057377 | A1 | 3/2006 | Harrison et al. |
| 2006/0094320 | A1 | 5/2006 | Chen et al. |
| 2006/0128012 | A1 | 6/2006 | Arinzeh et al. |
| 2006/0198865 | A1* | 9/2006 | Freyman et al. ............... 424/423 |
| 2006/0204539 | A1 | 9/2006 | Atala |
| 2006/0240064 | A9 | 10/2006 | Hunter et al. |
| 2007/0179594 | A1 | 8/2007 | Llanos et al. |
| 2007/0267725 | A1 | 11/2007 | Lee et al. |
| 2008/0009599 | A1* | 1/2008 | East et al. ......................... 528/1 |
| 2008/0112150 | A1 | 5/2008 | Jones |
| 2008/0206343 | A1 | 8/2008 | Edinger et al. |
| 2008/0246126 | A1 | 10/2008 | Bowles et al. |
| 2009/0028921 | A1 | 1/2009 | Arinzeh |
| 2009/0048358 | A1 | 2/2009 | Kim |
| 2009/0325296 | A1 | 12/2009 | Arinzeh et al. |
| 2010/0078771 | A1 | 4/2010 | Barth et al. |
| 2010/0078776 | A1 | 4/2010 | Barth et al. |
| 2010/0173158 | A1 | 7/2010 | Furuzono et al. |
| 2010/0233234 | A1 | 9/2010 | Arinzeh et al. |
| 2010/0233807 | A1 | 9/2010 | Arinzeh et al. |
| 2010/0274742 | A1 | 10/2010 | Hodjat |
| 2010/0324697 | A1 | 12/2010 | Arinzeh et al. |
| 2011/0300626 | A1 | 12/2011 | Arinzeh |
| 2013/0052254 | A1 | 2/2013 | Arinzeh et al. |

OTHER PUBLICATIONS

Tim Hardingham, "Proteoglycans: Their Structure, Interactions and Molecular Organization in Cartilage," Biochemical Society Transactions, vol. 9, No. 6, pp. 489-497 (1981).*

Friedenstein, A. et al., Bone Marrow Osteogenetic Stem Cells: In Vitro Cultivation and Transplantation in Diffusion Chambers, Cell Tissue Kinet, 1987, 20(3):263-72.

Safronova, E. E. et al., Characteristics of the macromolecular components of the extracellular matrix in human hyaline cartilage at different stages of ontogenesis, Biomedical Science, 1991, 2:162-8.

Haynesworth, S. et al., Cell Surface Antigens on Human Marrow-Derived Mesenchymal Stem Cells are Detected by Monoclonal Antibodies, J. Cell Physiol., 1992, 138:8-16.

Rickard, D. J. et al., Induction of rapid osteoblast differentiation in rat bone marrow stromal cell cultures by dexamethason and BMP-2, Dev. Bio., 1994, 161:218-28.

Jaiswal, N. et al., Osteogenic differentiation of purified culture-expanded human mesenchymal stem cells in vitro, J. Cell Biochem., 1997, 64:295-312.

Kadiyala, S. et al., Culture-expanded, bone marrow-derived mesenchymal stem cells can regenerate a critical-sized segmental bone defect, Tissue Engineering, 1997, 3(2):173-85.

Mackay, A. M. et al., Chondrogenic differentiation of cultured human mesenchymal stem cells from marrow, Tissue Engineering, 1998, 4(4):415-28.

Brudner, S. P. et al., Bone Regeneration by Implantation of Purified, Culture-Expanded Human Mesenchymal Stem Cells, J. Orthop. Res., 1998, 16:155-62.

Praemer, A., Musculoskeletal conditions in the United States, American Academy of Orthopaedic Surgeons, 1999, p. 34-9.

Pittenger, M. F. et al., Multilineage potential of adult human mesenchymal stem cells, Science, 1999, 284:143-7.

Browne, J. E. et al., Surgical alternatives for treatment of articular cartilage lesions, J. Am. Acad. Orthop. Surg., 2000, 8(3):180-9.

Xie, L. et al., A niche maintaining germ line stem cells in the *Drosophila* ovary, Science, 2000, 290(5490):328.

Fuchs, E. et al., Stem cells: a new lease on life, Cell, 2000, 100:143-55.

Watt, F. M. et al., Out of eden: stem cells and their niches, Science, 2000, 287(5457):1427.

DeLise, A. M. et al. Cellular interactions and signaling in cartilage development, Osteoarthritis and Cartilage, 2000, 8:309-34.

Christensen, N. D. et al., Papillomavirus microbicidal activities of high-molecular-weight cellulose sulfate, dextran sulfate, and polystyrene sulfonate, Antimicrobial Agents and Chemotherapy, 2001, 45(12):3427-32.

Ishihara, M. et al., Heparin-carrying polystyrene (HCPS)-bound collagen substratum to immobilize heparin-binding growth factors and to enhance cellular growth, J. Biomed. Mat. Res., 2001, 56(4):536-44.

Rogovina, S. Z. et al., Solid state production of cellulose-chitosan blends and their modification and the diglycidyl ether of oligo(ethylene oxide), Polymer Degradation and Stability, 2001, 73(3):557-60.

Barry, F. et al., Chondrogenic differentiation of mesenchymal stem cells from bone marrow: differentiation-dependent gene expression of matrix components, Experimental Cell Research, 2001, 268:189-200.

Dozin, B. et al., Response of young, aged and osteoarthritic human articular chondrocytes to inflammatory cytokines: molecular and cellular aspects, Matrix Biology, 2002, 21(5):449-59.

Anderson, R. A. et al., Preclinical evaluation of sodium cellulose sulfate (Ushercell) as a contraceptive antimicrobial agent, Journal of Andrology, 2002, 23(3):426-38.

Arinzeh, T. et al.,In vivo evaluation of a bioactive scaffold for bone tissue engineering, J. Biomed. Mat. Res., 2002, 62:1-13.

Muller, P. Y. et al., Processing of gene expression data generated by quantitative real-time RT-PCR, Biotechniques, 2002, 32(6):1372-4.

Nettles et al., Potential Use of Chitosan as a Cell Scaffold Material for Carilage Tissue Engineering, Tissue Engineering, Vo. 8, No. 6, pp. 1009-1016, 2002.

Endres et al., Osteogenic Induction of Human Bone Marrow-Derived Mesenchymal Progenitor Cells in Novel Synthetic Polymer-Hydrogel Matrices, Tissue Engineering, vol. 9, No. 4, pp. 689-702, 2003.

Arinzeh, T. et al, Allogeneic mesenchymal stem cells regenerate bone in a critical-sized canine segmental defect, Journal of Bone and Joint Surgery American, 2003, 85-A(1):1927-35.

Sittinger et all., Current Strategies for Cell Delivery in Cartilage and Bone Regeneration, Current Opinion in Biotechnology, vol. 115, Issue 5, pp. 411-418, 2004.

Shields, K. J. et al., Mechanical properties and cellular proliferation of electrospun collagen Type II, Tissue Engineering, 2004, 10(9-10)1510-7.

You, J. O. et al., Calcium-alginate nanoparticles formed by reverse microemulsion as gene carriers, macromolecular Symposia, 2004, 219(147):153.

Browne, J. E. et al., Clinical outcome of autologous chondrocyte implantation at 5 years in US subjects, Clinical Orthopaedics and Related Research, 2005, 436:237-45.

(56) References Cited

OTHER PUBLICATIONS

Kang, S. W. et al., Ply(lactic-co-glycolic acid) microspheres as an injectible scaffold for cartilage tissue engineering, Tissue Engineering, 2005, 11(3-4):438-47.
Clar, C. at al., Clinical and cost-effectiveness of autologous chondocyte implantation for cartilage defects in knee joints: systematic review and economic evaluation, Health Technology Assessment, 2005, 9(47):four pages.
Maire, M. et al., Retention of transforming growth factor using functionalized dextran-based hydrogels, Biomaterials, 2005, 26(14):1771-80.
Schaffellner, S. et al., Porcine islet cells microencapsulated in sodium cellulose sulfate, Transplantation Proceedings, 2005, 37(1):248-52.
Li, W. J. et al., Multilineage differentiation of human mesenchymal stem cells in a three-dimensional nanofibrous scaffold, Biomaterials, 2005, 26(5):5158-66.
Kuo, C. K. et al., Cartilage tissue engineering: its potential and uses, Current Opinion in Rheumatology, 2006, 18(1):64-73.
Pelttari, K. et al., Premature induction of hypertrophy during in vitro chondrogenesis of human mesenchymal stem cells correlates with calcification and vascular invasion after ectopic transplantation in SCID mice, Arthritis and Rheumatism, 2006, 54:3254-66.
Shanmugasundaram, S. et al., The Effect of Varying the Architecture of Scaffolds on Mesenchymal Stem Cell Osteogenesis and Chondrogenesis, Transactions of the 2006 Annual Meeting of the Society for Biomaterials, 2006.
Gama, C. L., Sulfation patterns of glycosaminoglycans encode molecular recognition and activity, Nature Chemical Biology, 2006, 2(9):467-73.
Stiegler, P. B. et al., Cryopreservation of insulin-producing cells microencapsulated in sodium cellulose sulfate, Transplantation Proceedings, 2006, 38(9):3026-30.
Li, W. J. et al., Fabrication and characterization of six electrospun poly(alpha-hydroxyester)-based fibrous scaffolds for tissue engineering applications, Acta Biomaterialia, 2006, 2(4):377-85.
Karlsson, C. et al., Differentiation of human mesenchymal stem cells and articular chondrocytes: analysis of chondrogenic potential and expression pattern of differentiation-related transcription factors, Journal of Orthopaedic Research, 2007, 25:152-63.
Chamberlain, G. et al., Concise review: mesenchymal stem cells: their phenotype, differentiation capacity, immunological features, and potential for homing, Stem Cells, 2007, 25(11):2739-49.
Xin, X. et al., Continuing differentiation of human mesenchymal stem cells and induced chondrogenic and osteogenic lineages in electrospun PLGA nanofiber scaffold, Biomaterials, 2007, 28(2):316-25.
Greco, S. et al., An interdisciplinary approach and characterization of neuronal cells transdifferentiated from human mesenchymal stem cells, Stem cells and development, 2007, 16(5):811-26.
Temple, M. M. et al., Age- and site-associate biomechanical weakening of human articular cartilage of the femoral condyle, Osteoarthritis and Cartilage, 2007, 15:1042-52.
Lack, S. et al:, High-resolution nuclear magnetic resonance spectroscopy studies of polysaccharides crosslinked by sodium trimetaphosphate: a proposal for the reaction mechanism, Carbohydrate Research, 2007, 342(7):943-53.
Collins, M. N. et al., Comparison of the effectiveness of four different crosslinking agents with hyaluronic acid hydrogel films for tissue-culture applications, Journal of Applied Polymer Science 2007, 104(5):3183-91.
Greco, S. J. et al., Functional similarities among genes regulated by oct-4 in human mesenchymal and embryonic stem cells, Stem Cells, 2007, 25(12:3143-54.
Mueller, M. B. et al., Functional characterization of hypertrophy in chondrogenesis of human mesenchymal stem cells, Arthritis and Rheumatism, 2008, 58(5):1377-88.
Forsten-Williams, K., et al., Control of growth factor networks by heparin sulfate proteoglycans, Annals of Biomedical Engineering, 2008, 36(12):2134-48.

Magnussen, R. A. et al., Treatment of focal articular cartilage defects in the knee: a systematic review, Clinical Orthopaedics and Related Research, 2008, 466(4):952-62.
Chondrogen clinical trial information for the treatment of knee injuries, Osiris Therapeutics, Inc., 2008, Ref. Type: Internet Communication.
Liu, Z. et al., Polysaccharides-based nanoparticles as drug delivery systems, Advanced Drug Delivery Reviews, 2008, 60(15):1650-62.
Bian, L. et al., Influence of chondoitin sulfate on the biochemical, mechanical and frictional properties of cartilage explants in long-term culture, Journal of Biomechanics, In press 2008.
Chen, Y. et al., Development of a chitosan-based nanoparticle formulation for delivery of a hydrophilic hexapeptide, dalargin, Biopolymers, 2008, 90(5):663-70.
Shanmugasundaram, S. et al., Regulation of human mesenchymal stem cell chondrogenesis by scaffold geometry and mechanical properties, Society for Biomaterials Annual Meeting, 2009.
Shanmugasundaram, et al., Microscale Versus Nanoscale Scaffold Architecture for Mesenchymal Stem Cell Chondrogenesis, Tissue Engineering: Part A, vol. 60, No. 00, 2010, pp. 1-10.
Davis, et al., Structural and Dielectric Investigation on the Nature of the Transition in a Copolymer of Vinylidene Fluoride and Trifluoroethylene, Macromolecules, 15: 329-333, 1982.
Lovinger, Ferroelectric Polymers, Science, New Series, vol. 220, No. 4602, pp. 1115-1121, 1983.
Patel, et al., Perturbation of the Direction of Neurite Growth by Pulsed and Focal Electric Fields, Journal of Neurosci, vol. 4, pp. 2939-47, 1984.
Humphrey, et al., The Dielectric Piezoelectric and Pyroelectric Properties of VDF-TrFE Copolymers, Plessey Research (Caswell) Limited, Allen Clark Research Centre, Caswell, Towcester, Northants, NN12 8EQ, England, 1986.
Borgens, Electric Fields in Vertebrate Repair, Natural and Applied Voltage in Vertebrate Regeneration and Hearling, Wiley-Liss, 1989.
Sambrook et al., Molecular Cloning: A Laboratory Manual, $2^{nd}$ 3d., Cold Spring Harbor Laboratory, Cold Spring Harbor Laboratory Press, Cold Springs Harbor, NY, 1989. (cover page and Table of Contents for vols. 1-3).
Koga, et al., Crystallization, Field-Induced Phase Transformation, Thermally Induced Phase Transition, and Piezoelectric Activity in P(Vinylidene Fluoride-TrFE) Copolymers with High Molar Content of Vinylidene Fluoride, J. Appl. Phys, 67(2), pp. 965-974, 1990.
Valentini, Electrically Charged Polymeric Substrates Enhance Nerve-Fiber Outgrowth in Vitro, Biomaterials, vol. 13, pp. 183-90, 1992.
Ausubel, et al., Current Protocols in Molecular Biology, John Wiley & Sons, New York, NY, 1993. (cover page and Table of Contentst).
Ohigashi, et al., Formation of "Single Crystalline Films" of Ferroelectric Copolymers of Vinylidene Fluoride and Trifluoroethylene, Appl. Phys. Lett., 66(24), pp. 3281-3283, 1995.
Kapur, et al, Human Monocyte Morphology is Affected by Local Substrate Charge Heterogeneity, J, Biomed Mater. Res., 32: 133, 1996. (abstract only).
Kapur., et al., Fabrication and Selective Surface Modification of 3-Dimensionally Textured Biomedical Polymers from Etched Silicon Substrates, Journal of Biomedical Materials Research, vol. 33, pp. 205-216, 1996.
Bouaziz, et al., Vascular Endothelial Cell Responses to Different Electrically Charged Poly(Vinylidene Fluoride) Supports Under Static and Oscillating Flow Conditions, Biomaterials, vol. 18, No. 2, 107-112, 1997.
Christie, et al., Ferroelectric and Piezoelectric Properties of a Quenched Poly(Vinylidene Fluoride-Trifluoroethylene) Copolymer, Journal of Polymer Science: Part B: Polymer Physics, vol. 35, 2671-2679, 1997.
Furukawa, Structure and Functional Properties of Ferroelectric Polymers, Advances in Colloid and Interface Science, 71-72; 183-208, 1997.
Miraglia, S. "A Novel Five-Transmembrane Hematopoietic Stem Cell Antigen: Isolation, Characterization, and Molecular Cloning," *Blood* 90:5013-21, 1997.

(56) References Cited

OTHER PUBLICATIONS

Omote, et al., Temperature Dependence of Elastic, Dielectric, and Piezoelectric Properties of "Single Crystalline" Films of Vinylidene Fluoride Trifluoroethylene Copolymer, J. Appl. Phys., 81(6), pp. 2760-2769, 1997.
Schmidt, et al., Stimulation of Neurite Outgrowth Using an Electrically Conducting Polymer, Proc. Natl. Acad. Sci, vol. 94, pp. 8948-8953, 1997.
Virts, E. et al. "Murine Mast Cells and Monocytes Express Distinctive Sets of CD45 Isoforms," *Immunology* 34(16-17):1119-97, 1997.
Yin, A.H. "AC133, A Novel Marker for Human Hematopoietic Stem and Progenitor Cells," *Blood* 90:5002-12, 1997.
Bune, et al., Two-Dimensional Ferroelectric Films, Nature, vol. 391, 874-877, 1998.
Zhao, et al., Electromechanical Properties of Electrostrictive Poly(Vinylidene Fluoride-Trifluoroethylene) Copolymer, Applied Physics Letters, vol. 73, No. 14, pp. 2054-2056, 1998.
Borgens, Electrically Mediated Regeneration and Guidance of Adult Mammalian Spinal Axons into Polymeric Channels, Neuroscience, 91(1):251-64; 1999.
Laurencin, C.T. "Tissue Engineering: Orthopedic Applications," *Ann. Rev. Biomed. Eng'g* 1:19-46, 1999.
Sittinger et al., Joint cartilage regeneration by tissue engineering, Z. Rheumatol, 58:130-5, 1999.
Hilczer, et al., The Method of Matching Resonance Frequencies in Coupled Transmitter PVDF/TRFE Diaphragms, IEEE Transactions on Dielectrics and Electrical Insulation, vol. 7, No. 4, pp. 498-502, 2000.
Ponticello et al., Gelatin-Based Resorbable Sponge As A Carrier Matrix For Human Mesenchymal Stem Cells in Cartilage Regeneration Therapy, *J Biomed Materials Res* 52: 246-255, 2000.
Brook et al., Columns of Schwann Cells Extruded Into the CNS Induce In-Growth of Astrocytes To Form Organized New Glial Pathways, GLIA, 33:118-130, 2001.
Guo et al., Biological features of mesenchymal stem cells from human bone marrow, Chinese Med J.. 114:9503, 2001.
Harrison, et al., Piezolelectric Polymers, ICASE, NASA Langley Research Center, Hampton, Virginia, NASA/CR-2001-211422, ICASE Report No. 2001-43, pp. 1-26, 2001.
Koombhongse, et al., Flat Polymer Ribbons and Other Shapes by Electrospinning, Journal of Polymer Science: Part B: Polymer Physics, vol. 39, 2598-2606, 2001.
Kotwal, et al., Electrical Stimulation Alters Protein Adsorption and Nerve Cell Interactions With Electrically Conducting Biomaterials, Biomaterials, 22: 1055-1064, 2001.
N.S.C.I.A., Spinal Cord Injury Fact Sheet, Birmingham, 2001; http://users.erols.com/nscia/resource/factshts/.
Negishi, Optic Nerve Regeneration Within Artificial Schwann Cell Graft in The Adult Rat, Brain Research Bulletin, 55:409-419, 2001.
Ploss, et al., Poling Study of PZT/P(VDF-TrFE) Composites, Composites Science and Technology, 61, 957-962, 2001.
Rahman et al., Enhancement of Chondrogenic Differentiation of Human Articular Chondrocytes by Biodegradable Polymers, Tissue Engineering, 7:781-90, 2001.
Yannas IV, Tissue and Organ Regeneration in Adults, Springer, 2001. (cover page and Table of Contents).
Li et al., Electrospun Naofibrous Structure: A Novel Scaffold For Tissue Engineering, Journal of Biomedical Materials Research, vol. 60, No. 4, pp. 613-621, 2002.
Benz, et al., Determination of the Crystalline Phases of Poly(Vinylidene Fluoride) Under Different Preparation Conditions Using Differential Scanning Calorimetry and Infrared Spectroscopy, Journal of Applied Polymer Science, vol. 89, 1093-1100, 2003.
Li, et al., Biological Response of Chondrocytes Cultured in Three-Dimensional Nanofibrous Poly(ϵ-caprolactone) Scaffolds, J. Biomed. Mat. Res. Part A., 67A, 4, pp. 1105-1114, 2003.
Livingston, et al., Mesenchymal Stem Cells Combined With Biphasic Calcium Phosphate Ceramics Promote Bone Regeneration, Journal of Materials Science: Materials in Medicine, 14: 211-218, 2003.
Luu et al., "Development of a Nanostructured DNA Delivery Scaffold via Electrospinning of PLGA and PLA-PEG block copolymers". Journal of Controlled Release, vol. 89, pp. 341-353, 2003.
Murphy et al., Stem Cell Therapy in A Caprine Model Of Osteoarthritis, *Arthritis Rheumatism* 48: No. 12, 3464-3474, 2003.
Sachlos, et al., Making Tissue Engineering Scaffolds Work, Review of the Application of Solid Freeform Fabrication Technology to the Production of Tissue Engineering Scaffolds, *European Cells & Materials* 5: 29-40, 2003.
Seoul, et al., Electrospinning of Poly(Vinylidene Fluoride)/Dimethylformamide Solutions With Carbon Nanotubes, Journal of Polymer Science: part B: Polymer Physics, vol. 41, 1572-1577, 2003.
Sikavitsas et al., "Mineralized Matrix Deposition By Marrow Stromal Osteoblasts in 3D Perfusion Culture Increases With Increasing Fluid Shear Forces". PNAS, vol. 100, No. 25, pp. 14683-14688, Dec. 9, 2003.
Wan-Ju, et al., Biological Response of Chondrocytes Cultrued in Three-Dimensional Nanofibrous Poly(-caprolactone) Scaffolds, J. Biomed. Mater. Res. 67A:1105-1114, 2003.
Yeh, E.T.H. et al., "Transdifferentiation of Human Peripheral Blood CD34+-Enriched Cell Population Into Cardiomyocytes, Endothelial Cells, and Smooth Muscle Cells in Vivo," Circulation 108:2070-73, 2003.
Yoshimoto et al., A Biodegradable Nanofiber Scaffold by Electrospinning and its Potential for Bone Tissue Engineering, Biomaterials, 24, pp. 2077-2082, 2003.
Zong et al., Electrospun Non-woven Membranes As Scaffolds For Heart Tissue Constructs. $226^{th}$ ACS National Meeting, 2003.
Bhattarai, et al., Novel Biodegradable Electrospun Membrance: Scaffold for Tissue Engineering, Biomaterials, vol. 25, No. 13, pp. 2595-2602, 2004.
Bryan, et al., Enhanced Peripheral Nerve Regeneration Through A Poled Bioresorbable Poly(Lactic-co-glycolic Acid) Guidance Channel, J. Neural Eng., 1, 91-98, 2004.
Dezawa, Specific Induction of Neuronal Cells From Bone Marrow Stromal Cells and Application for Autologous Transplantation, Journal of Clinical Investigation; 113:1701-1710, 2004.
Jin et al., "Human Bone Marrow Stromal Cell Responses On Electrospun Silk Fibroin Mats", Biomaterials, vol. 25, pp. 1039-1047, 2004.
Li et al., Carbon Nanotubes Induced Nonisothermal Crystallization of Ethylene-Vinyl Acetate Copolymer, Materials Letter, 58, pp. 3967-3970, 2004.
Rosenzweig, et al., Rodent Models for Treatment of Spinal Cord Injury: Research Trends and Progress Toward Useful Repair, Current Opinion in Neurology, 17(2), 121-31, 2004.
Shanmugasundaram, et al., Applications of Electrospinning: Tissue Engineering Scaffolds and Drug Delivery System, Bioengineering, Proceedings of the Northeast Conference, vol. 30, pp. 140-141, 2004.
Shin et al., In Vivo Bone Tissue Engineering Using Mesenchymal Stem Cells on a Novel Electrospun Nanofibrous Scaffold, Tissue Engineering, 10, pp. 33-41, 2004.
Wei et al., Structural and Properties of Nano-Hydroxyapatite/Polymer Composite Scaffolds for Bone Tissue Engineering, Biomaterials, 25, pp. 4749-4757, 2004.
Arinzeh et al., A Comparative Study of Biphasic Calcium Phosphate Ceramics for Human Mesenchymal Stem-Cell-induced Bone Formation, Biomaterials, 26(17): 3631-8, 2005.
Aroen, A. et al, "Articular Cartilage Defects in a Rabbit Model, Retention Rate of Periosteal Flap Cover", Acta Orthrop. 76(2):220-4, 2005.
Cummings, et al., Human Neural Stem Cells Differentiate and Promote Locomoter Recovery in Spinal Cord-Injured Mice, Proceedings of the National Academy of Sciences, 102(39):14069-74, 2005.
Ducharme, et al., Ferroelectric Polymeric Langmuir-Blodgett Films for Non-Volatile Memory Applications, Nebraska Research Initiative, the National Science Foundation and the Office of Naval Research, Department of Physics and Astronomy and the Center for Materials Research and Analysis at the University of Nebraska, Lincoln, NE, pp. 1-41, 2005.
Fujihara, et al., Guided Bone Regeneration Membrane Made of Polycaprolactone/Calcium Carbonate Composite Nano-fibers, Biomaterials, 26, pp. 4139-4147, 2005.

(56) References Cited

OTHER PUBLICATIONS

Holmes, N. "CD45: All is Not Yet Crystal Clear", Immunology 117:145-155, 2005.
Klein, et al., Influence of Composition on Relaxor Ferroelectric and Electromechanical Properties of Poly(Vinyliden Fluoride-Trifluoroethylene-Chlorofluoroethylene), Journal of Applied Physics, 97, 094105, pp. 1-4, 2005.
Laxminarayana, et al., Functional Nanotube-Based Textiles: Pathyway to Next Generation Fabrics With Enhanced Sensing Capabilities, Textile Res. J., 75(9), 670-680, 2005.
Livingston, et al., A Comparative Study of Biphasic Calcium Phosphate Ceramics for Human Mesenchymal Stem-Cell-Induced Bone Formation, Biomaterials, 26, pp. 3631-3638, 2005.
Montjovent et al., Biocompatibility of Bioresorbable Poly(L-lactic acid) Composite Scaffolds Obtained by Supercritical Gas Foaming With Human Fetal Bone Tissue Engineering 11, pp. 1640-1649, 2005.
Naber, et al., Low-Voltage Programmable Ferroelectric Polymer Field-Effect Transistors, Applied Physics Letters, 87: 203509, pp. 51-57, 2005.
Shapiro, et al., Oscillating Field Stimulation for Complete Spinal Cord Injury in Humans: A Phase 1 Trial, Journal of Neurosurgery Spine, 2(1):3-10, 2005.
Wutticharoenmongkol, et al., Electrospinning of Polystyrene/Poly(2-methoxy-5-(2'-ethylhexyloxy)-1,4-phenylene Vinylene) Blends, Journal of Polymer Science: Part B: Polymer Physics, vol. 43, pp. 1881-1891, 2005.
Wutticharoenmongkol, Preparation and Characterization of Novel Bone Scaffolds Based on Electrospun Polycaprolactone Fibers Filled with Nanoparticles, Macromolecular Bioscience, vol. 6, pp. 70-77, 2005.
Zhang et al., Tissue-Engineering Approaches for Axonal Guidance, Brain Res. Brain Res. Rev, vol. 49, pp. 48-64, 2005.
Zhao, et al., Preparation and Properties of Electrospun Poly(Vinylidene Fluoride) Membranes, Journal of Applied Polymer Science, vol. 97, 466-474, 2005.
Beloti, et al., In Vitro Biocompatibility of a Novel Membrane of the Composite Poly(Vinylidene-Trifluoroethylene)/Barium Titanate, InterScience Journal of Biomedical Materials Research Part A, 281-288, 2006.
Cizkova, et al., Transplants of Human Mesenchymal Stem Cells Improve Functional Recovery After Spinal Cord Injury in the Rat, Cellular and Molecular Neurobiology, 26(7/8):1167-80, 2006.
Georgiou et al., Polyactic Acid-Phosphate Glass Composite Foams as Scaffolds for Bone Tissue Engineering, J. Biomed. Mat. Res. Part B: Applied Biomaterials, Published Online Jul. 12, 2006.
Himes, et al., Recovery of Function Following Grafting of Human Bone Marrow-Derived Stromal Cells Into the Injured Spinal Cord, Neurorehabilitation and Neural Repair, 20:278-96, 2006.
Hung, et al., The Effect of Chitosan and PVDF Substrates on the Behavior of Embryonic Rat Cerebral Cortical Stem Cells, Biomaterials, 27, 4461-4469, 2006.
Nasir, et al., Control of Diameter, Morphology, and Structure of PVDF Nanofiber Fabricated by Electrospray Deposition, Journal of Polymer Science: Part B: Polymer Physics, vol. 44, 779-786, 2006.
Oudega, et al., Schwann Cell Transplantation for Repair of the Adult Spinal Cord, Journal of Neurotrauma, 23(3-4), 453-67, 2006.
Rezwan et al., Biodegradable and Bioactive Porous Polymer/inorganic Composite Scaffolds for Bone Tissue Engineering, Biomaterials, 27, pp. 3413-3431, 2006.
Tashiro, et al, Structural Correlation Between Crystal Lattice and Lamellar Morphology in the Ferroelectric Phase Transition of Vinylidene Fluoride-Trifluoroethylene Copolymers as Revealed by the Simultaneous Measurements of Wide-Angle and Small-Angle X-Ray Scatterings, Polymer, 47, 5433-5444, 2006.
Thomas et al., Electrospun Bioactive Nanocomposite Scaffolds of Polycaprolactone and Nanohydroxyapatite for Bone Tissue Engineering, Journal of Nanoscience Nanotechnology, 6(2), pp. 487-493, 2006.
Wu, et al., Poly(Vinylidene Fluoride)/Polyethersulfone Blend Membranes: Effects of Solvent Sort, Polyethersulfone and Polyvinylpyrrolidone Concentration on Their Properties and Morphology, Journal of Membrane Science, 285, 290-298, 2006.
Wutticharoenmongkol et al., Preparation and Characterization of Novel Bone Scaffolds Based on Electrospun Polycaprolactone Fibers Filled with Nanoparticles, Macromol. Biosci. 6, pp. 70-77, 2006.
Wutticharoenmongkol, et al., Novel Bone Scaffolds of Electrospun Polycaprolactone Fibers Filled With Nanoparticles, Journal of Nanoscience Nanotechnology, 6(2), pp. 514-522, 2006.
Yang, et al., Preparation of Bioelectret Collagen and Its Influence on Cell Culture In Vitro, J. Mater. Sci: Mater Med, 17:767-771, 2006.
Catalani, et al., Evidence for Molecular Orientation and Residual Charge in the Electrospinning of Poly (Butylenes Terephthalate) Nanofibers, Macromolecules, vol. 40, pp. 1693-1697, 2007.
Greiner, et al, Electrospinning: A Fascinating Method for the Preparation of Ultrathin Fibers, Angewandte Chemie Int. Ed. Engl. 46: 5670-5703, 2007.
Huang, Isothermal Crystallization of High-Density Polyethylene and Nanoscale Calcium Carbonate Composites, Journal of Applied Science, 107, pp. 3163-3172, 2007.
Miyazaki, et al., Crystallization Rate of Amorphous Nifedipine Analogues Unrelated to the Glass Transition Temperature, Interational Journal of Pharmaeceutics, 336, pp. 191-195, 2007.
Osiris Therapeutics Announces Positive One Year Data from Chondrogen Trial for Knee Repair, Osiris Therapeutics, Inc., Ref. Type: Internet Communication, 2007.
http://stemcells.nih.gov/info/scireport/appendixE.asp, (visited Dec. 28, 2007. last visited Aug. 25, 2011), 6 pages.
Sun, et al. Crystallization and Thermal Properties of Polyamide 6 Composites Filled With Different Nanofillers, Materials Letters, 61, pp. 3963-3966, 2007.
Venugopal et al., Biocomposite Nanofibres and Osteoblasts for Bone Tissue Engineering, Nanotechnology, 18, pp. 1-8, 2007.
Wi, et al., Characterization of Poly(Vinylidene Fluoride-Trifluoroethylene) 50/50 Copolymer Films as a Gate Dielectric, J. Mater Sci: Mater Electron, pp. 1-6, 2007.
Zhou et al., In Vitro Bone Engineering Based on Polycaprolactone and Polycaprolactone-Tricalcium Phosphate Composites, Polym. Int. 56, pp. 333-342, 2007.
Duffell., et al., Long-Term Intensive Electrically Stimulated Cycling by Spinal Cord-Injured People: Effect on Muscle Properties and Their Relation to Power Output, Muscle and Nerve, 38:1304-11, 2008.
Kim, et al., The Role of Aligned Polymer Fiber-Based Constructs in the Bridging of Long Peripheral Nerve Gaps, Biomaterials, 29(21):3117-27, 2008.
Lankford, et al., Olfactory Ensheathing Cells Exhibit Unique Migratory, Phagocytic and Myelinating Properties in the X-Irradiated Spinal Cord Not Shared by Schwann Cells, Glia, (epub ahead of print), 2008.
PCT International Search Report and Written Opinion for PCT/US2005/043876 dated Jun. 25, 2008.
PCT International Search Report and Written Opinion for PCT/US2008/067322 dated Sep. 29, 2008.
European Search Report dated Dec. 9, 2009 for PCT/US2005/043876.
ISP Dec. 24, 2008 for PCT/US2008/067322.
IPRP Dec. 22, 2009 for PCT/US2008/067322.
PCT International Search Report and Written Opinion for PCT/US2012/050156 dated Feb. 1, 2013.
European Patent Office Action for European Patent Application No. 05852938.9 dated Jul. 1, 2014.
U.S. Appl. No. 14/381,496, filed Aug. 27, 2014.

* cited by examiner a. chitosan b. D-glucosamine  c. N-Acetyl-D-glucosamine

CARTILAGE REPAIR SYSTEMS AND APPLICATIONS UTILIZING A GLYCOSAMINOGLYCAN MIMIC

CROSS REFERENCE TO RELATED APPLICATIONS

This application claims the benefit under 35 U.S.C. §119 (e) of U.S. Provisional Application No. 61/329,172; titled "Cartilage Repair Systems and Applications Utilizing a Glycosaminoglycan Mimic," filed Apr. 29, 2010; and is a Continuation-in-Part of U.S. patent application Ser. No. 12/661,242; titled: "System and Method for a Hydrogel and Hydrogel Composite for Cartilage Repair Applications," filed Mar. 12, 2010, which are both incorporated herein by reference in their entirety.

FIELD OF THE INVENTION

This invention relates to the fields of biotechnology, and regenerative medicine. More specifically, it relates to cell and tissue scaffolding, tissue repair.

BACKGROUND

Articular cartilage has a limited intrinsic ability to heal. For this reason, orthopaedic management of these lesions remains a persistent problem for the orthopedist and patient. The importance of treating injury to articular cartilage is underscored by the fact that several million people are affected in the United States alone by cartilage damage. (See Praemer A, Furner S, Rice D P. Musculoskeletal conditions in the United States. *American Academy of Orthopaedic Surgeons* 1999 p. 34-9). Focal lesions of articular cartilage can progress to more widespread cartilage destruction and arthritis that is disabling. Thus, numerous procedures have been developed in an attempt to treat these lesions and halt or slow the progression to diffuse arthritic changes. (See Browne J E, Branch T P. Surgical alternatives for treatment of articular cartilage leasions. *J Am Acad Orthop Surg* 2000; 8(3):180-9).

Surgical procedures to restore articular cartilage include debridement, abrasion arthroplasty, microfracturing, autologous chondrocyte transplantation and osteoarticular transfer. (Browne J E, Anderson A F, Arciero R, Mandelbaum B, Moseley J B, Micheli L J, Fu F, Erggelet C. Clinical outcome of autologous chondrocyte implantation at 5 years in US subjects. *Clinical Orthopaedics and Related Research* 2005; 436:237-245; Magnussen R A, Dunn W R, Carey J L, Spindler K P. Treatment of focal articular cartilage defects in the knee: a systematic review. *Clinical Orthopaedics and Related Research* 2008; 466:952-96). At present, none of these techniques have been able to restore a normal cartilaginous surface and have suffered from poor integration with the surrounding normal articular cartilage. Frequently, the repair tissue has inferior biochemical and biomechanical properties.

Current tissue engineering methods are aimed at filling the cartilage defects with cells or scaffolds alone, or in combination with one another. (Kang S W, Jeon O, Kim B S. Poly (lactic-co-glycolic acid) microspheres as an injectable scaffold for cartilage tissue engineering. *Tissue Engineering* 2005; 11:438-447; Kuo C K, Li W J, Mauck R L, Tuan R S. Cartilage tissue engineering: its potential and uses. *Current Opinion in Rheumatology* 2006; 18:64-73). However, it appears that the absence of cells leads to a poor quality reparative tissue.

Autologous chondrocytes are FDA approved, but of major concern is the limited proliferative capacity of differentiated chondrocytes (Dozin B, Malpeli M, Camardella L, Cancedda R, Pietrangelo A. Response of young, aged and osteoarthritic human articular chondrocytes to inflammatory cytokines: molecular and cellular aspects. *Matrix Biology* 2002; 21:449-459). Long-term studies in patients have demonstrated that treated defects are filled with fibrocartilage, which may account for the poor mechanical stability. (Clar C, Cummins E, McIntyre L, Thomas S, Lamb J, Bain L, Jobanputra P, Waugh N. Clinical and cost-effectiveness of autologous chondrocyte implantation for cartilage defects in knee joints: systematic review and economic evaluation. *Health Technology Assessment* 2005; 9:1-8). Therefore, adult stem cells have been sought as an alternative cell source.

Mesenchymal stem cells (MSCs) are multipotent cells that are capable of differentiating into osteoblasts, chondrocytes, adipocytes, tenocytes, myoblasts, and neural cell lineages. (Pittenger M F, Mackay A M, Beck S C, Jaiswal R K, Douglas R, Mosca J D, Moorman M A, Simonetti D W, Craig S, Marshak D R. Multilineage potential of adult human mesenchymal stem cells. *Science* 1999; 284:143-147). From a small, bone marrow aspirate obtained from adults, MSCs can be isolated, readily expanded due to their proliferative capacity, and characterized. (Friedenstein A, Chailakhyan R, Gerasimov U V. Bone Marrow Osteogenic Stem Cells: In Vitro Cultivation and Transplantation in Diffusion Chambers. *Cell Tissue Kinet* 1987; 20:263-72; Haynesworth S, Baber M, Caplan A. Cell Surface Antigens on Human Marrow-Derived Mesenchymal Stem Cells are Detected by Monoclonal Antibodies. *J Cell Physiol* 1992; 138:8-16). In vitro and in vivo analyses have demonstrated that culture expanded MSCs can maintain the capacity to differentiate and proliferate after extensive passaging (Jaiswal N, Haynesworth S E, Caplan A I, Bruder S P. Osteogenic differentiation of purified culture-expanded human mesenchymal stem cells in vitro. *J Cell Biochem* 1997; 64:295-312; Kadiyala S, Jaiswal N, Bruder S P. Culture-expanded, bone marrow-derived mesenchymal stem cells can regenerate a critical-sized segmental bone defect. *Tissue Engineering* 1997; 3:173-185; Rickard D J, Sullivan T A, Shenker B J, Leboy P S, Kazhdan I. Induction of rapid osteoblast differentiation in rat bone marrow stromal cell cultures by dexamethason and BMP-2. *Dev Bio* 1994; 161:218-228), suggesting that MSCs may be valuable as a readily available and abundant source of cells in the tissue engineering field. Allogeneic MSCs are also currently in clinical trials for various disorders or conditions. Therefore, an allogeneic MSC approach for tissue regeneration, e.g., cartilage tissue regeneration, could provide an excellent off-the-shelf therapy.

One way for a biodegradable scaffold to be successful is to make the material's rate of degradation commensurate with the growth of new tissue, e.g., cartilage. Ideally, the scaffold degrades at a rate to substantially maintain structural support during the initial stages of formation, but also allows space for continuous growth of new tissue. In addition to biochemical stability, the ideal synthetic tissue scaffold would also provide an appropriate chemical environment to facilitate cell and tissue growth, repair, and/or regeneration, and at the same time, provide the necessary biomechanical stability. It is therefore of great importance to develop a scaffold that will address these issues and provide the appropriate cues to support growth and differentiation of the stem cells, e.g., MSCs.

SUMMARY

It has been surprisingly and unexpectedly discovered that hydrophilic or water soluble polysaccharide (e.g, cellulose) hydrogels can form biochemically and biomechanically stable scaffolds or attachment supports capable of facilitating or enhancing the growth and/or differentiation of progenitor or stem cells (e.g., MSCs). Accordingly, compostions and methods for supporting, facilitating or enhancing cell growth and/or differentiation are taught and described herein. In addition, the hydrogel compositions described herein are easy to apply in vitro or in vivo, and integrate with the surrounding host tissue. For example, the hydrogel or scaffold compositions can be pre-formed and shaped prior to use or they can be applied or administered in situ directly to the site of the defect. Therefore, the hydrogel compositions taught and described herein are also suitable for use in tissue engineering or as an implantable material to promote, facilitate, and/or enhance tissue growth, regeneration, and/or repair.

Thus, in one aspect, a synthetic hydrogel polymer network or scaffold is taught and described, which surprisingly and unexpectedly mimics the natural gel-like medium of the ECM. The hydrogel comprises a network of polymers or microfibrils comprising a hydrophilic or water soluble polysaccharide compound. In certain embodiments, the soluble polysaccharide compound is a water soluble cellulose compound. In certain embodiments, the water soluble cellulose compound is an anionic, water soluble cellulose.

In any of the hydrogel or scaffold embodiments taught or described herein, the ionic, water soluble cellulose compound comprises an anionic, water soluble cellulose compound, such as, by way of non-limiting example, cellulose sulfate (e.g., sodium cellulose sulfate (NaCS)) or cellulose phosphate (e.g., sodium cellulose phosphate (NaCP)). When combined with an aqueous solution the anionic, water soluble cellulose compound forms a hydrogel polymer network. In certain embodiments, the present invention utilizes sodium cellulose sulfate (NaCS) as a polymer network forming material. In additional embodiments, the effective amount of water soluble cellulose used to form the hydrogel or scaffold is from about 0.01% to about 20% (w/w) with respect to the final weight of the hydrogel. In additional embodiments, the amount of water soluble cellulose used is about 0.01, 0.1, 0.5, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, or 20.0% (w/w), and including all values in between.

In any of the hydrogel or scaffold embodiments taught or described herein may also further comprise an additional ingredient, such as, e.g., a cell, collagen, a growth factor, a proteoglycan, a non-functional soluble polysaccharide, an excipient, carrier or adjuvant, or combinations thereof. In an additional aspect, a hydrogel or scaffold as taught and described herein comprises an isolated differentiable progenitor or stem cell, e.g., a MSC isolated from a mammal such as a human, seeded onto the hydrogel wherein the hydrogel supports, promotes, facilitates and/or enhances the growth and/or differentiation of the cell. In certain embodiments the hydrogel or scaffold is seeded with a MSC or population of MSCs and promotes chondrogenesis; i.e., the differentiation of the MSC into a chondrocyte or a cell that displays a chondrocyte-like phenotype. Furthermore, in still other embodiments, the non-functional soluble polysaccharide is dextran.

In another aspect, the hydrogel or scaffold as taught and described herein further comprises a matrix or mesh of substantially insoluble fibers or filaments. In certain embodiments, the hydrogel comprises a polymeric network of an ionic, water soluble cellulose compound, and an polyionic polysaccharide, e.g., a polycationic polysaccharide, e.g., chitosan, in an amount sufficient to form a fibrous or filamentous mesh or matrix within the hydrogel. In certain embodiments, the polycationic polysaccharide is chitosan. In additional embodiments, the effective amount of chitosan included ranges from about 0.01% to about 20% (w/w) with respect to the weight of the hydrogel. In additional embodiments, the percent of chitosan included is about 0.01, 0.1, 0.5, 1.0, 2.0, 3.0, 4.0, 5.0, 6.0, 7.0, 8M, 9.0, 10.0, 11.0, 12.0, 13.0, 14.0, 15.0, 16.0, 17.0, 18.0, 19.0, or 20.0% (w/w), and including all values in between. In certain embodiments, the chitosan has a molecular weight of from about 100 kilodalton (kDa) to about 350 kDa. In other embodiments, the chitosan has a molecular weight of from about 150 kDa to about 325 kDa. In additional embodiments, the chitosan has a molecular weight of from 190 kDa to about 310 kDa.

In additional embodiments, the amount of polycationic polysaccharide added to the hydrogel is sufficient to produce interfiber spaces comprising an average size of from about 1 µm to about 1 mm or more. In other embodiments, the amount of polycationic polysaccharide, e.g., chitosan, added to the hydrogel is sufficient to produce interfiber spaces comprising an average size of about 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, and/or 1000 microns, including all values in between, and combinations thereof.

In any of the hydrogel or scaffolds taught or described herein, including hydrogels comprising a fiber matrix, the hydrogels or scaffolds further comprise a complexing or stabilizing agent, for example, a counter-ion (anion or cation) or chemical cross-linker. The complexing or stabilizing agent confers additional biochemical and/or biomechanical stability or both to the hydrogel by interacting or complexing with the cellulose polymers, e.g., via hydrophobic, covalent, ionic, hydrogen, Van der Waals forces or other chemical bond. In certain embodiments, the hydrogel or scaffold comprises an anionic cellulose compound, e.g., NaCS or NaCP, and a cation. In certain embodiments, the cation comprises a divalent cation, such as, e.g., calcium, magnesium, manganese, or iron(II).

In additional embodiments, the hydrogel or scaffold comprises an ionic, water soluble cellulose compound and a chemical cross-linking agent. A wide variety of suitable chemical cross-linking agents are known in the art. For example, suitable cross-linking for use in the hydrogels described herein include those that react with, e.g., amines, sulfate groups, hydroxyl groups, glycosidic bonds, such as, e.g., polydiallyl dimethyl ammonium chloride (PDADMAC) and bisepoxides. In certain embodiments the cross-linking agent is a diglycidyl ether, e.g., diisosorbide bisepoxide. In certain embodiments, the effective amount of complexing or cross-linking agent added is from about 0.01% to about 20% (w/w) with respect to the weight of the hydrogel. In additional embodiments, the amount of complexing or cross-linking agent included is about 0.01, 0.1, 0.5, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, or 20.0% (w/w), and including all values in between.

In another aspect, a hydrogel or scaffold for use in tissue engineering or an implantable material is taught and described that comprises at least two polysaccharides, such as, e.g., two water soluble cellulose compounds. In certain embodiments, the compounds are cross-linked as described herein, e.g., by means of ionic or chemical interactions.

In another aspect, taught and described herein are methods for preparing a hydrogel or scaffold to facilitate cell growth and differentiation or tissue regeneration and repair, e.g., cartilage repair, the method comprising the steps combining or admixing an aqueous solution and an effective amount of an ionic, water soluble cellulose compound, wherein the combination forms a hydrogel capable of acting as a support for the growth and/or differentiation of a cell, e.g., a progenitor or stem cell. In certain embodiments, the method further comprises a step of adding an effective amount of a polycation, a cation, a chemical cross-linker or a combination thereof, as taught and described herein. In additional embodiments, the method further comprises a step of adding an isolated, differentiable progenitor or stem cell, e.g., a MSC, wherein the cell grows and/or differentiates on the hydrogel or scaffold. In still another embodiment, the isolated, differentiable progenitor or stem cell differentiates on the hydrogel or scaffold into a chondrocyte and/or a cell displaying a chondrocyte-like phenotype.

In another aspect, methods of treating and/or repairing a tissue, e.g., cartilage tissue, in a subject are taught and described, the method comprising administering to a subject an effective amount of a hydrogel or scaffold as taught and described herein, wherein the hydrogel or scaffold is effective for supporting, promoting, and/or enhancing the growth, regeneration, and/or repair of the tissue. In certain embodiments, the method further comprises a step of seeding a progenitor or stem cell, e.g., MSC, onto the hydrogel either prior or subsequent to administering the hydrogel to the subject.

In another aspect, methods of treating arthritis are taught and described, the method comprising administering to a subject an effective amount of a hydrogel or scaffold as described herein wherein the hydrogel or scaffold is effective for alleviating or ameliorating the symptoms of arthritis in the subject. In certain embodiments, the method further comprises a step of seeding a progenitor or stem cell, e.g., MSC, onto the hydrogel either prior or subsequent to administering the hydrogel to the subject.

In another aspect, a cell culture media is taught and described, the cell culture media comprising an aqueous solution, and an effective amount of an ionic, water soluble polysaccharide, and optionally a pH buffer. In an embodiment, the water soluble polysaccharide is an anionic, water soluble cellulose compound, e.g., NaCS or NaCP or both. In another embodiment, the cell culture media comprises from about 0.01% to about 5% (w/w) of an anionic water soluble cellulose compound. In another embodiment, the cell culture media comprises from about 0.01% to about 0.5% (w/w) of an anionic water soluble cellulose compound. In another embodiment, the cell culture media further comprises an additional ingredient, such as, e.g., a cell, collagen, a growth factor, a proteoglycan, a non-functional soluble polysaccharide, an excipient, carrier or adjuvant, or combinations thereof. In certain embodiments, the growth factor is transforming growth factor beta (TGF-β). In still another embodiment the TGF-β is TGF-β3.

In another aspect, a method for culturing a progenitor or stem cell, e.g., MSC, is taught and described, the method comprising providing at least one isolated differentiable progenitor or stem cell, and culturing the cell in a cell culture media as taught and described herein. In certain embodiments the progenitor cell is an MSC, and the cell culture media promotes and/or enhances the growth and/or differentiation of the cell into a chondrocyte or a cell displaying a chondrocyte-like phenotype.

The preceding general areas of utility are given by way of example only and are not intended to be limiting on the scope of the present disclosure and appended claims. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional objects and advantages are expressly included within the scope of the present invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

DETAILED DESCRIPTION

Figure 1:
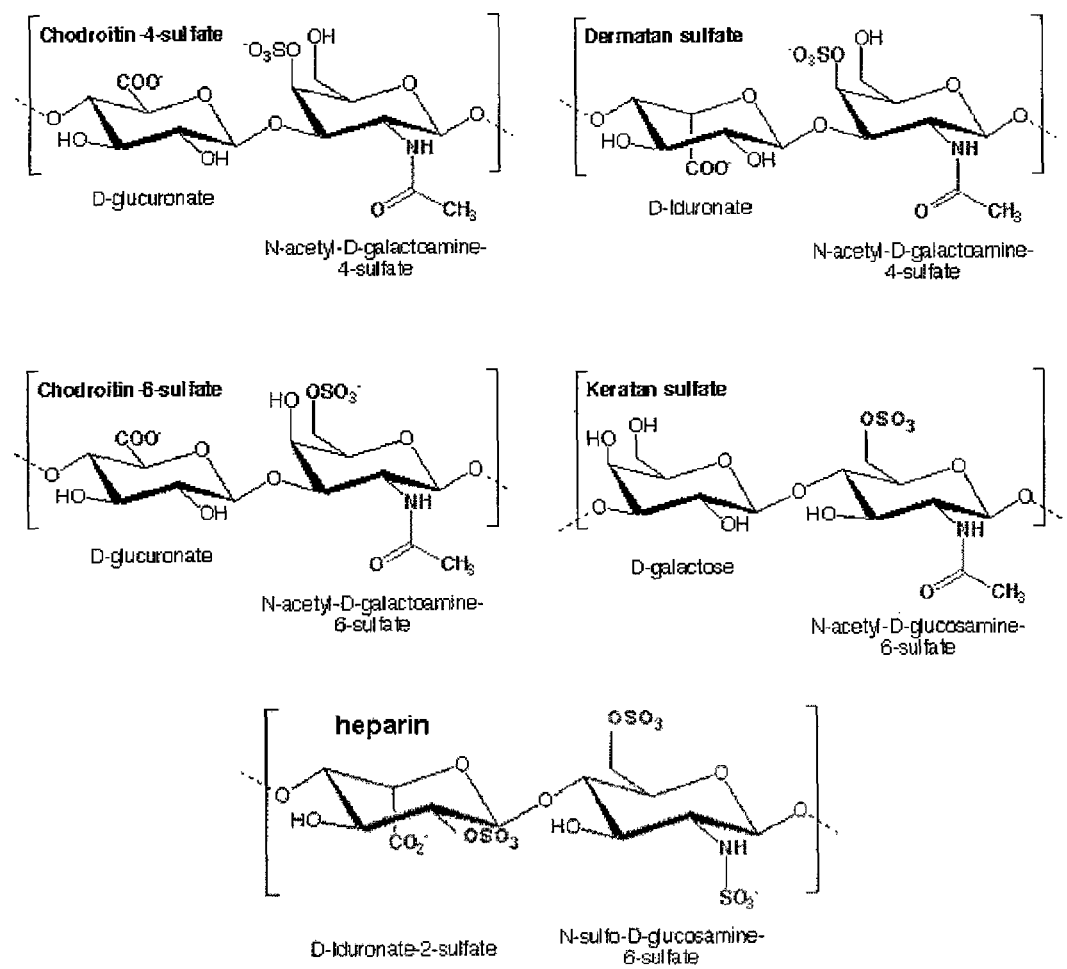
FIG. 1 shows the structure of several glycosaminoglycans.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

This application claims the benefit under 35 U.S.C. §119 (e) of U.S. Provisional Application No. 61/329,172, titled "Cartilage Repair Systems and Applications Utilizing a Glycosaminoglycan Mimic," filed Apr. 29, 2010; which is incorporated herein by reference in its entirety. The present disclosure is related in certain respects to U.S. patent application Ser. No. 12/661,242, titled: "System and Method for a Hydrogel and Hydrogel Composite for Cartilage Repair Applications," filed Mar. 12, 2010, the disclosure of which is incorporated herein by reference in its entirety.

As used herein, and unless specified otherwise, the terms "hydrogel" and "scaffold," can mean but are in no way limited to, the hydrogel compositions taught and described herein, which comprise a network of polymers comprising an ionic, water soluble polysaccharide, e.g., cellulose (e.g., NaCS or NaCP).

The term "cell" can mean, but is in no way limited to, its usual biological sense, and does not refer to an entire multicellular organism. The cell can, for example, be in viva, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The term "cellulose" can mean, but is in no way limited to, its usual biological sense. Cellulose is an organic compound with the formula $(C_6H_{10}O_5)_n$, a polysaccharide consisting of, e.g., a linear chain of several hundred to over ten thousand $\beta(1 \rightarrow 4)$linked D-glucose units.

As used herein, the terms "bioactive" and "bioactivity" are used interchangeably, and can mean but are in no way limited to, any effect on, interaction with, or response from living tissue.

As used herein, the term "biocompatible material" can mean but is in no way limited to, a material that the body generally accepts without a major immune response, which is capable of implantation in biological systems, for example, tissue implantation, without causing excessive fibrosis or rejection reactions. As used herein, the term "biodegradable" refers to the ability of a substance or material to break down into harmless substances by the action of living organisms.

As used herein, the phrase "ionic water soluble cellulose compounds," can mean but is in no way limited to, a family of hydrophilic cellulose compounds that are long chain macromolecules of repeating glucose units (i.e., polymers) substituted to varying extents with ionic groups, e.g., anionic groups. For example, in certain exemplary embodiments, the anionic group is at least one of a sulfate ($-SO_3^-$; e.g., sodium cellulose sulfate) or a phosphate ($-PO_3^-$; e.g., sodium cellulose phosphate). Molecular weights of water soluble cellulose compounds encompassed by the invention typically range from about $5 \times 10^5$ to about $3 \times 10^6$ g/mol. The hydroxyl groups of each glucose unit can be substituted with from one to three ionic groups, e.g., sulfate groups. The ion substitution (e.g., sulfation) imparts water solubility to the otherwise insoluble cellulose. The availability of unsubstituted hydroxyl groups also provides reactive sites for crosslinking for the soluble cellulose, e.g., cellulose sulfate. For example, a negatively charged sulfate group is balanced by the positive charge of a cationic species, typically an alkali metal cation, and preferably the sodium cation.

As used herein, the term "collagen," can mean but is in no way limited to, any of a family of extracellular, closely related proteins occurring as a major component of connective tissue, giving it strength and flexibility. At least 14 types exist, each composed of tropocollagen units that share a common triple-helical shape but that vary somewhat in composition between types, with the types being localized to different tissues, stages, or functions. In some types, including the most common, Type I, the tropocollagen rods associate to form fibrils or fibers; in other types the rods are not fibrillar but are associated with fibrillar collagens, while in others they form nonfibrillar, nonperiodic but structured networks. Tropocollagen, the basic structural unit of collagen comprises a helical structure consisting of three polypeptide chains, each chain composed of about a thousand amino acids, coiled around each other to form a spiral and stabilized by inter- and intra-chain covalent bonds. It is rich in glycine, which occurs as nearly one residue out of three, as well as proline, hydroxyproline, and hydroxylysine; the last two rarely occur in other proteins.

As used herein, the term "polymer," can mean but is in no way limited to, a macromolecule formed by the chemical union of five or more identical combining units called monomers. In most cases, the number of monomers is quite large and often is not precisely known. In synthetic polymers, this number may be controlled to a predetermined extent. Combinations two, three, or four monomers are called, respectively, dimers, trimers, and tetramers, and are known collectively as oligomers. Polymers may be inorganic (e.g., siloxane, sulfur chains, black phosphorus, boron-nitrogen, silicones) or organic (meaning containing carbon). Organic polymers may be natural [e.g., polysaccharides, such as starch, cellulose, pectin, seaweed gums, vegetable gums; polypeptides, such as casein, albumin, globulin, keratin, insulin, DNA; and hydrocarbons], synthetic [such as thermoplastics (unvulcanized elastomers, nylon, polyvinyl chloride, linear polyethylene, polystyrene, polypropylene, polyurethane, acrylate resins); thermosetting (e.g., vulcanized elastomers, crosslinked polyethylene, phenolics, alkyds, polyesters), and semisynthetic (e.g., cellulosics, such as rayon, methylcellulose, cellulose acetate; and modified starches)].

As used herein, the term "homopolymer," can mean but is in no way limited to, a natural or synthetic polymer derived from a single monomer.

As used herein, the term "polysaccharide," can mean but is in no way limited to, a long-chain natural or synthetic polymer made up of linked simple sugars (monosaccharides) such as glucose and/or related molecules (e.g., glucuronate, galactose, galactosamine, glucosamine, acetyl glucosamine). Two monosaccharide molecules may be joined by a glycosidic bond to form a disaccharide, as, for instance, in the linkage of glucose and fructose to create sucrose. More complicated polysaccharides such as starch, glycogen, cellulose or chitin consist of numerous monosaccharide units joined by glycosidic bonds.

As used herein, the term "stem cells," can mean but is in no way limited to, undifferentiated cells having high proliferative potential with the ability to self-renew that may migrate to areas of injury and may generate daughter cells that may undergo terminal differentiation into more than one distinct cell phenotype. These cells have the ability to differentiate into various cells types and thus promote the regeneration or repair of a diseased or damaged tissue of interest. The term "cellular differentiation" refers to the process by which cells acquire a cell type. The term "progenitor cell" as used herein refers to an immature cell in the bone marrow that may be isolated by growing suspensions of marrow cells in culture dishes with added growth factors. Progenitor cells are referred to as colony-forming units (CFU) or colony-forming cells (CFC). The specific lineage of a progenitor cell is indicated by a suffix, such as, but not limited to, CFU-F (fibroblastic). A progenitor cell, like a stem cell, has a the ability to differentiate into a specific type of cell, but is already more specific than a stem cell and is pushed to differentiate into its "target" cell. Generally, stem cells can replicate indefinitely, whereas progenitor cells can only divide a limited number of times.

As used herein, the terms "osteoprogenitor cells", "mesenchymal cells", "mesenchymal stem cells (MSC)", or "marrow stromal cells" are used interchangeably to refer to multipotent stem cells that differentiate from CFU-F cells capable of differentiating along several lineage pathways into osteoblasts, chondrocytes, myocytes and adipocytes. When referring to bone or cartilage, MSCs commonly are known as osteochondrogenic, osteogenic, chondrogenic, or osteoprogenitor cells, since a single MSC has shown the ability to differentiate into chondrocytes or osteoblasts, depending on the medium.

As used herein, the term "chondrocytes" as used herein, can mean but is in no way limited to, cells found in cartilage that produce and maintain the cartilaginous matrix. From least to terminally differentiated, the chondrocytic lineage is (i) colony-forming unit-fibroblast (CFU-F); (ii) mesenchymal stem cell/marrow stromal cell (MSC); (3) chondrocyte. The term "chondrogenesis" refers to the formation of new cartilage from cartilage forming or chondrocompetent cells.

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" can mean, but is in no way limited to, a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size.

The term "down-regulate" can mean, but is in no way limited to, the expression of a gene, or level of RNAs or equivalent RNAs encoding one or more proteins, or activity of one or more proteins is reduced below that observed in the absence of an agent provided by the invention. For example, the expression of a gene can be decreased in order to treat, prevent, ameliorate, or modulate a pathological condition caused or exacerbated by high levels of gene expression.

The term "up-regulate" can mean, but is in no way limited to, the expression of a gene, or level of RNAs or equivalent RNAs encoding one or more protein subunits, or activity of one or more protein subunits is greater than that observed in the absence of an agent provided by the invention. For example, the expression of a gene can be increased in order to treat, prevent, ameliorate, or modulate a pathological condition caused or exacerbated by an absence or low level of gene expression.

By "modulate" can mean, but is in no way limited to, that the expression of the gene, or level of RNAs or equivalent RNAs encoding one or more proteins, or activity of one or more proteins is up-regulated or down-regulated, such that the expression, level, or activity is greater than or less than that observed in the absence of an agent provided by the invention.

The term, "gene" can mean, but is in no way limited to, a nucleic acid that encodes RNA, for example, nucleic acid sequences including but not limited to a segment encoding a polypeptide.

It must be noted that as used herein and in the appended claims, the singular forms "a", "and", and "the" include plural references unless the context clearly dictates otherwise. All technical and scientific terms used herein have the same meaning. Efforts have been made to ensure accuracy with respect to numbers used (e.g. amounts, temperature, etc.) but some experimental errors and deviations should be accounted for, and is implied by the use of the word "about." Unless indicated otherwise, parts are parts by weight, molecular weight is weight average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In the body, adult stem cells are often localized to specific chemically and topologically complex microenvironments, or so-called "niches". Increasing experimental evidence supports the notion that stem cells can adjust their properties according to their surroundings, and select specific lineages according to the cues they receive from their niche. (Fuchs E, Segre J. Stem cells: a new lease on life. *Cell* 2000; 100:143-155; Watt F M, Hogan B L M. Out of eden: stem cells and their niches. *Science* 2000; 287:1427). In order for a stem cell therapy to be successful in the repair of a specific tissue type, the microenvironment of the cells should be designed to relay the appropriate chemical and physical signals to them. Mimicking characteristics of the microenvironment during cartilage development may be a viable approach. During cartilage development, one of the earliest events is pre-cartilage mesenchymal cell aggregation and condensation resulting from cell-cell interaction, which is mediated by both cell-cell and cell-matrix adhesion (fibronectin, proteoglycans, hyaluronic acid and collagens). (DeLise A M, Fischer L, Tuan R S. Cellular interadctions and signaling in cartilage development. *Osteoarthritis and Cartilage* 2000; 8:309-334). Multiple growth factors and morphogens such as Wnts, transforming growth factor-beta (TGF-β), and fibroblast growth factors (FGF) are also present contributing to the regulation of the differentiation process. These growth factors interact with key matrix molecules such as proteoglycans, which are composed of glycosaminoglycans, that play an important role in regulating the half-life of the growth factors and providing prolonged activity. (Hubbell J A. Materials as morphogenetic guides in tissue engineering. *Current Opinion in Biotechnology* 2003; 14:551-558). During cartilage development, chondroitin-6-sulfate and heparin sulfate are the predominate glycosaminoglycans present (Lash J W, Saxen L, Kosher R A. Human chondrogenesis: glycosaminoglycan content of human embryonic cartilage. *Journal of Experimental Zoology* 1974; 189:127-131) and recent work has demonstrated that growth factor binding to these molecules is strictly controlled by their pattern and degree of sulfation. (Gama C L, Tully S E, Sotogaku N, Clark P M, Rawat M, Vaidehi N. Sulfation patterns of glycosaminoglycans encode molecular recognition and activity. *Nature Chemical Biology* 2006; 2:467-473). It has been observed that receptor binding of growth factors is regulated by the interactions with sulfated glycosaminoglycans. (Forsten-Williams K, Chu C L, Fannon M, Buczek-Thomas J A, Nugent M A. Control of growth factor networks by heparan sulfate proteoglycans. *Annals of Biomedical Engineering* 2008; 36:2134-2148).

There are two principal structural features of the ECM: a nano-fibrous network or framework composed of protein filaments to which cells can attach, and a hydrated, gel-like medium supported by this network through which soluble nutrients can diffuse. In the natural ECM, the hydrogel component has the structural role of mediating compressive stress. The hydrogel consistency is maintained by proteoglycans, which are composed of glycosaminoglycans. These glycosaminoglycans impart a functional aspect to the hydrogel. The functional role of glycosaminoglycans in the extracellular matrix is to complex and sequester specific proteins such as growth factors. Further, the sequestered protein along with the GAG forms a triad complex with a tyrosine kinase receptor at the plasma membrane of the cell to initiate cells response to the presence of the growth factor. (See Forsten-Williams). FIG. 1 shows the structure of several glycosaminoglycans.

Proteoglycans are glycoproteins that are heavily glycosylated. The basic proteoglycan unit consists of a "core protein" with one or more covalently attached glycosaminoglycan (GAG) chain(s). The point of attachment is a serine residue to which the glycosaminoglycan is joined through a tetrasaccharide bridge (For example: chondroitin sulfate-GlcA-Gal-Gal-Xyl-PROTEIN). The Ser residue is generally in the sequence -Ser-Gly-X-Gly- (where X can be any amino acid residue), although not every protein with this sequence has an attached glycosaminoglycan. The chains are long, linear carbohydrate polymers that are negatively charged under physiological conditions, due to the occurrence of sulfate and uronic acid groups. Proteoglycans occur in the connective tissue, and are a major component of the animal extracellular matrix (ECM). Here they form large complexes, both to other proteoglycans, to hyaluronan and to fibrous matrix proteins (such as collagen). They are also involved in binding cations (such as sodium, potassium and calcium) and water, and also regulating the movement of molecules through the matrix. Evidence also shows they can affect the activity and stability of proteins and signalling molecules within the matrix. Individual functions of proteoglycans can be attributed to either the protein core or the attached GAG chain and serve as lubricants.

Proteoglycans can be categorised depending upon the nature of their glycosaminoglycan (GAG) chains. Proteoglycans can also be categorised by size (kDa). Types include: decorin, biglycan, versican, testican, perlecan, neurocan, aggrecan (the major proteoglycan in cartilage), fibromodulin, and lumican. Protein cores made in the rough endoplasmic reticulum are posttranslationally modified by glycosyltransferases in the Golgi apparatus, where GAG disaccharides are added to protein cores to yield proteoglycans; the exception is the GAG hyaluronan, which is uniquely synthesized without a protein core and is "spun out" by enzymes at the cell surface directly into the extracellular space. The GAGs extend perpendicularly from the core in a brush-like structure. The linkage of GAGs to the protein core involves a specific trisaccharide composed of two galactose residues and a xylose residue (GAG-GalGalXyl-O—$CH_2$-protein). The trisaccharide linker is coupled to the protein core through an O-glycosidic bond to a Serine residue in the protein. Some forms of keratan sulfates are linked to the protein core through an N-asparaginyl bond. The protein cores of proteoglycans are rich in S and T residues, which allows multiple GAG attachments.

The most abundant heteropolysaccharides in the body are the glycosaminoglycans (GAGs). The majority of GAGs in the body are linked to core proteins, forming proteoglycans (also called mucopolysaccharides). GAGs are long unbranched polysaccharides consisting of a repeating disaccharide unit. The repeating unit consists of a hexose (six-carbon sugar) or a hexuronic acid, linked to a hexosamine (six-carbon sugar containing nitrogen). For example, the disaccharide units contain either of two modified sugars, N-acetylgalactosamine (GalNAc) or N-acetylglucosamine (GlcNAc), and a ironic acid such as glucuronate or iduronate. GAGs are located primarily on the surface of cells or in the extracellular matrix (ECM). In naturally occurring ECM, GAGs are highly negatively charged molecules, with extended conformation that imparts high viscosity to the solution. Along with the high viscosity of GAGs comes low compressibility, which makes these molecules ideal for a lubricating fluid in the joints. At the same time, their rigidity provides structural integrity to cells and provides passageways between cells, allowing for cell migration.

Water is strongly absorbed by GAGs; this is where the resistance to pressure comes from. The density of sugar molecules and the net negative charges attract cations, for example, $Na^+$, which, after the sodium binds, attracts water molecules. Some examples of glycosaminoglycan uses in nature include heparin as an anticoagulant, hyaluronan as a component in the synovial fluid lubricant in body joints, and chondroitins, which can be found in connective tissues, cartilage, and tendons. Members of the glycosaminoglycan family vary in the type of hexosamine, hexose or hexuronic acid unit they contain (e.g. glucuronic acid, iduronic acid, galactose, galactosamine, glucosamine). (Table I). They also vary in the geometry of the glycosidic linkage.

The specific GAGs of physiological significance are hyaluronic acid, dermatan sulfate, chondroitin sulfate, heparin, heparan sulfate, and keratan sulfate. Although each of these GAGs has a predominant disaccharide component (see Table I, below), heterogeneity does exist in the sugars present in the make-up of any given class of GAG. In certain embodiments, this disclosure provides a hydrogel comprising a polymer network comprising compounds that mimic the naturally occurring GAGs (e.g., those listed in Table I).

As used herein, "chondrocyte-like" can mean but is in no way limited to, a cell that demonstrates a phenotype (e.g., based on markers of gene expression, activity, and/or morphology) that is consistent with that of a chondrocyte or a cell progressing through various stages of differentiation on the chondrocyte lineage.

In one aspect, a synthetic hydrogel or scaffold is taught and described, which surprisingly and unexpectedly mimics the natural gel-like medium of the ECM. Typical synthetic hydrogels lack functional sites that would enable interaction with proteins present in the media of cell growth cultures or the in

TABLE 1

Examples of GAGs.

| Name | Hexuronic acid/Hexose | Hexosamine | Linkage geometry between predominant monomeric units | Unique features |
| --- | --- | --- | --- | --- |
| Chondroitin sulfate | GlcUA or GlcUA(2S) | GalNAc or GalNAc(4S) or GalNAc(6S) or GalNAc(4S,6S) | -4GlcUAβ1-3GalNAcβ1- | Most prevalent GAG |
| Dermatan sulfate | GlcUA or IdoUA or IdoUA(2S) | GalNAc or GalNAc(4S) or GalNAc(6S) or GalNAc(4S,6S) | -4IdoUAβ1-3GalNAcβ1- | Distinguished from chondroitin sulfate by the presence of iduronic acid, although some hexuronic acid monosaccharides may be glucuronic acid. |
| Keratan sulfate | Gal or Gal(6S) | GlcNAc or GlcNAc(6S) | -3Gal(6S)β1-4GlcNAc(6S)β1- | Keratan sulfate type II may be fucosylated. |
| Heparin | GlcUA or IdoUA(2S) | GlcNAc or GlcNS or GlcNAc(6S) or GlcNS(6S) | -4IdoUA(2S)α1-4GlcNS(6S)α1- | Highest negative charge density of any known biological molecule |
| Heparan sulfate | GlcUA or IdoUA or IdoUA(2S) | GlcNAc or GlcNS or GlcNAc(6S) or GlcNS(6S) | -4GlcUAβ1-4GlcNAcα1- | Highly similar in structure to heparin, however heparan sulfates disaccharide units are organised into distinct sulfated and non-sulfated domains. |
| Hyaluronan | GlcUA | GlcNAc | -4GlcUAβ1-3GlcNAcβ1- | The only GAG that is exclusively non-sulfated |

One of the challenges in the art of regenerative medicine has been to develop a cost effective, synthetic cell/tissue hydrogel or scaffold that effectively mimics the fibrous and gel-like structural elements of the ECM, in particular, the ECM of cartilage. However, surprisingly and unexpectedly, the novel hydrogels or scaffolds described herein mimic the natural extracellular matrix (ECM), and when combined with progenitor or stem cells, supports and promotes cell differentiation. In certain aspects, the hydrogels or scaffolds described herein also comprise a fiber or filamentous matrix that further mimics the natural ECM environment, such as the ECM of cartilage.

Figure 2:
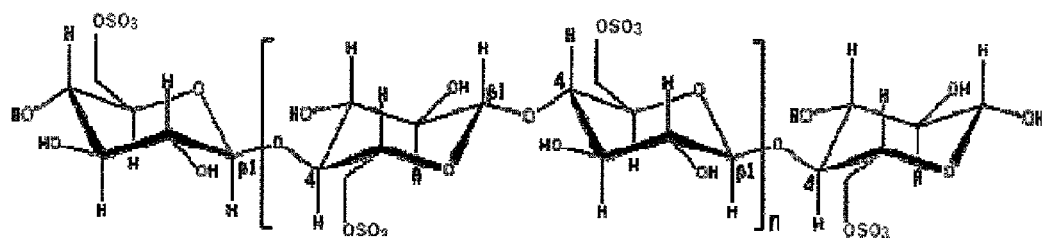
FIG. 2 shows a exemplary structure of a regular 6-substituted sodium cellulose sulfate (NaCS) compound. NaCS can be sysnthesized to have up to three sulfate groups per glucose residue (e.g., sulfation at one or more of positions 2, 3, and/or 6).

The present innovation is based on the surprising and unexpected discovery that hydrophilic or water soluble cellulose hydrogels can form biochemically and biomechanically stable scaffolds or attachment supports capable of facilitating and/or enhancing the growth, and/or differentiation of progenitor or stem cells (e.g., omnipotent, pluripotent, or multipotent, such as MSCs). Described herein are compostions and methods for supporting, promoting, and/or enhancing cell or tissue growth, differentiation, regeneration, and/or repair. As described below, culturing of a progenitor or stem cell, e.g., a MSC, on the hydrogel or scaffolds as provided by this disclosure supports and promotes condrogenesis (i.e., facilitates and/or enhances the growth and/or differentiation of the MSCs to a chondrocyte or to a cell displaying a condroncyte-like phenotype).

vivo milieu. The structure of glycosaminoglycans suggests that the presence of sulfate groups provide that functionality. Receptor binding of growth factors is regulated by the interactions with sulfated glycosaminoglycans. (See Forsten-Williams). Recent reports have suggested that the specific patterns of sulfation function as molecular recognition motifs that can only act with specific growth factors to mediate the cellular processes. (See Gama C L, Tully S E, Sotogaku N, Clark P M, Rawat M, Vaidehi N. Sulfation patterns of glycosaminoglycans encode molecular recognition and activity. Nature Chemical Biology 2006; 2(9):467-73). Similar behavior has yet to be reported for cellulose sulfate. Only functionalized dextran hydrogels containing sulfate groups have been reported, but only for the enhancement of osteoinductive potential of BMP. (See Maire M, Logeart-Avramoglou D, Degat M C, Chaubet F. Retention of transforming growth factor using functionalized dextran-based hydrogels. Biomaterials 2005; 26(14):1771-80). FIG. 2 shows the structure of a regular 6-substituted sodium cellulose sulfate (NaCS).

In one embodiment, the hydrogel or scaffold comprises an aqueous medium or solution, and a polymer network or microfibrils comprising a hydrophilic or water soluble polysaccharide compound. In certain embodiments, the soluble polysaccharide compound is an ionic, water soluble cellulose compound. In certain embodiments, the ionic water soluble cellulose compound is an anionic, water soluble cellulose. When combined with an aqueous solution the anionic, water soluble cellulose compound forms a hydrogel polymer network. In any of the hydrogel or scaffold embodiments taught or described herein, the ionic, water soluble cellulose compound that forms the polymer network comprises an anionic, water soluble cellulose compound, such as, for example, cellulose sulfate (e.g., sodium cellulose sulfate (NaCS)) or cellulose phosphate (e.g., sodium cellulose phosphate (NaCP)). An illustration of sodium cellulose sulfate is depicted in FIG. 2. In certain embodiments, the present invention utilizes sodium cellulose sulfate (NaCS) as a hydrogel material.

Cellulose can be modified, for example, by sulfation or phosphation, to convert it from an insoluble polysaccharide to an ionic, hydrophilic polysaccharide. Generally, cellulose can be modified at positions 2, 3, and/or 6 of the glucose units. Without being bound by any particular theory, the inventors hypothesize that cellulose having a 6-sulfated glucose unit aptly mimics the naturally occurring glycosaminoglycan 6-sulfonated glucuronate and acetyl galactosamine.

In certain embodiments, the hydrogel or scaffold comprises a polymer network comprising at least one anionic cellulose compound, wherein the anionic cellulose compound is NaCS or NaCP or both. The water soluble cellulose compounds of the present invention comprise about 6 wt % to about 21 wt % of sulfur or phosphate, respectively. In another embodiment, the anionic cellulose compound has, by weight, from about 6 wt % to about 12 wt % sulfate or phosphate, respectively, which corresponds to the incorporation of, on average, between zero and 1 sulfate or phosphate moiety at one of positions 2, 3, or 6 of the glucose units. In additional embodiments, the anionic cellulose compound has from 13 wt % to about 17 wt % sulfate or phosphate, respectively, which corresponds to the incorporation of, on average, from greater than one to two sulfate or phosphate moieties on the glucose units. In other embodiments, the anionic cellulose compound has from 18 wt % to about 21 wt % sulfate or phosphate, respectively, which corresponds to the incorporation of, on average, from greater than two to three sulfate or phosphate moieties on the glucose units. Preferably, the compounds comprise about 12 wt % to about 18 wt % of sulfur.

According to any of the hydrogel or scaffold embodiments taught or described herein, NaCS or NaCP is synthesized with varying degrees of substitution, i.e., sulfation or phosphation, respectively. Experimental testing for this, as well as other exemplary embodiments was done as follows: NaCS having varying levels of sulfation was synthesized from cellulose, cotton linters, according to previously reported methods. (Wang Z M, Li L, Zheng B S, Normakhamatoc N, Guo S Y. Preparation and anticoagulation activity of sodium cellulose sulfate. *International Journal of Biological Macromolecules* 2007; 41:376-382). The degree and position of sulfation was determined prior to comparison of embodiments. (Kowasaka K, Okajima K, Kamide K. Determination of the distribution of sustituent groups in sodium cellulose sulfate: assignment of $^1$H and $^{13}$C NMR peaks by two dimensional COSY and CH-Cosy Methods. *Polymer Journal* 1991; 23:823-836).

Thus, in certain embodiments, the hydrogel or scaffold as taught and described herein comprises a polymer network wherein the polymer network comprises a combination of cellulosic polymers with multiple degrees of sulfation, respectively. For example, in certain embodiments, the hydrogel comprises an aqueous solution and a plurality of anionic water soluble cellulose polymers sulfated to varying degrees, respectively. In other words, in certain embodiments the hydrogel or scaffold as taught and described herein comprises, in an aqueous solution, at least two of the following: a cellulose sulfate with about 6-12% sulfation (i.e., average of about 1 site sulfated), a cellulose sulfate with about 13-17% sulfation (i.e., average of about 2 sites sulfated), a cellulose sulfate with about 18-20% sulfation, or combinations thereof (i.e., average of about 3 sites sulfated).

In one embodiment, NaCS is used as the main hydrogel component. One commercially available NaCS has a sulfur level based on atomic mass of about 18%. This suggests that on average, each glucose residue in the polysaccharide is substituted with slightly more than two sulfate groups as shown in FIG. 2. At low concentration in aqueous media, NaCS forms a viscous solution. At higher concentrations, it forms a stiff gel. With respect to NaCS, preferably the solutions comprise from about 0.01 wt % to about 15 wt % of NaCS. More preferably, the solutions comprise from about 5 wt % to about 10 wt % of NaCS.

When hydrated the anionic, water soluble cellulose compound forms a hydrogel comprising a gel-like network of polysaccharide fibrils. In certain embodiments, the amount of water soluble cellulose used to form the hydrogel or scaffold is from about 0.01% to about 20% (w/w) with respect to the final weight of the hydrogel. In additional embodiments, the amount of water soluble cellulose included is about 0.01, 0.1, 0.5, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, or 20.0% (w/w), including all values in between.

The hydrogel or scaffold as described herein is useful as an injectable delivery system for use alone or in combination with other components. Therefore, in another aspect the disclosure provides a hydrogel adapaged for injection in vivo and/or in situ in a subject, wherein the hydrogel comprises an aqueous solution, and effective amount of an ionic, water soluble cellulose compound, and wherein the ionic, water soluble cellulose compound forms a polymer network that facilitates cell growth and/or differentiation. In an embodiment, the injectable hydrogel or scaffold comprises greater than about 0.01% (w/w) of an anionic, water soluble cellulose compound. In another embodiment, the injectable hydrogel or scaffold comprises from about 0.01% to about 20% (w/w) of an anionic, water soluble cellulose compound. Cellulose sulfate compounds can be synthesized on a commercial scale, and have an enormous advantage in cost and availability over other glycosaminoglycans. Thus, in any of the hydrogel embodiments described herein, a composition comprising sodium cellulose sulfate (NaCS) scaffold material is adapted for use as an injectable material for use in cartilage tissue repair. For example, NaCS can form a cross-linked hydrogel for use as an injectible delivery system for use alone or in combination with other components, such as cells, growth factors (e.g., cytokines and chemokines), polysaccharides, proteoglycans, GAGs, cross-linking agents or combinations thereof. In certain additional embodiments, the injectable hydrogel also comprises a fibrous mesh as a scaffold construct that more closely mimics the natural ECM of cartilage in both structure and function.

In another aspect, the hydrogel or scaffolds as taught and described herein further comprise a matrix or mesh of substantially insoluble fibers or filaments. It has been surprisingly and unexpectedly discovered that hydrogel or scaffold compositions as taught and described herein, which contain both fibrous and gel-like structural elements, aptly mimic the natural ECM, in particular, cartilage ECM, in both structure and function. For example, it was surprisingly and unexpectedly discovered that addition of a polycationic polysaccharide results in the spontaneous formation of nano- or micron-sized fibers or filaments arranged within the hydrogel network of ionic water soluble cellulose polymers. Thus, the hydrogel as taught and described herein can also be used in combination with a fibrous mesh, the mesh or matrix provides a scaffold or cell attachment surface supporting and promoting cell growth and/or differentiation, as well as tissue regeneration and repair.

In certain embodiments of this aspect, the hydrogel comprises a polymeric network of an ionic, water soluble cellulose compound, and a polycationic polysaccharide, e.g., chitosan or polycationic dextran such as diethylaminoethyl dextran, in a sufficient amount to form a fibrous or filamentous mesh or matrix within the hydrogel. Chitosan is a cationic polysaccharide comprised of d-glucosamine and N-acetyl-d-glucosamine subunits. The amine moieties remain protonated at slightly acidic pH and, therefore, is positively charged. Thus, without being bound by any particular theory, the inventors believe that chitosan forms fibers by forming ionic interactions with the negatively charged, anionic, cellulose polymers (i.e., polymeric coascervation), e.g., NaCS or NaCP. (See FIG. 6a). This effect has been observed with nanoparticles. (See Chen Y, Siddalingappa B, Chan P H, Benson H A. Development of a chitosan-based nanoparticle formulation for deliver of a hydrophilic hexapeptide, dalargin. *Biopolymers* 2008; 90(5):663-70).

In certain embodiments, the polycationic polysaccharide is chitosan. In additional embodiments, the amount of chitosan included is from about 0.01% to about 20% (w/w) with respect to the weight of the hydrogel. In a further embodiment, the chitosan has a molecular weight of from about 100 kDa to about 350 kDa. In another embodiment, the chitosan has a molecular weight of from about 150 kDa to about 325 kDa. In an additional embodiment, the chitosan has a molecular weight of from 190 kDa to about 310 kDa. In certain embodiments, the amount of chitosan included is about 0.01, 0.1, 0.5, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, or 20.0% (w/w), and including all values in between.

In additional embodiments, the amount of polycationic polysaccharide, e.g., chitosan, added to the hydrogel is sufficient to produce interfiber spaces comprising an average size of from about 1 μm to about 1 mm or more. In other embodiments, the amount of polycationic polysaccharide, e.g., chitosan, added to the hydrogel is sufficient to produce interfiber spaces comprising an average size of about 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, and/or 1000 microns, including all values in between, and combinations thereof.

In additional embodiments, the hydrogel or scaffold comprising a fiber matrix as taught and described herein, may further comprise a stem cell or progenitor cell, for example, a mesenchymal stem cell isolaged from a subject, e.g., a mammal such as a human. The hydrogel or scaffold having a fiber matrix embedded with stem cells promotes stem cell chrondrogenesis. The hydrogel or scaffold comprising a fiber matrix may also further comprise collagen, growth factor, or non-functional soluble polysaccharides, or combinations thereof. In a preferred embodiment, the non-functional soluble polysaccharide is dextran.

In any of the hydrogel or scaffolds taught or described herein, including hydrogels comprising a fiber matrix, the hydrogels or scaffolds further comprise a complexing or stabilizing agent, for example, a counter-ion (anion or cation) or chemical cross-linker, wherein the complexing or stabilizing agent is present at greater than or equal to 0.05% (w/w). Without being bound by any particular theory, the inventors believe that the complexing or stabilizing agent confers additional chemical and/or mechanical stability or both to the hydrogel by interacting or complexing with the cellulose polymers, e.g., via hydrophobic, covalent, ionic, hydrogen, Van der Waals forces or other chemical bond. (See, FIGS. 4 and 5). In certain embodiments, the hydrogel or scaffold comprises an anionic cellulose compound, e.g., NaCS or NaCP, and a cation. In certain embodiments, the cation comprises a divalent cation, such as, e.g., calcium, magnesium, manganese, or iron(II).

In another emobodiment of the present invention, NaCS gels will be cast from PBS solutions (in order maintain a pH of 7.4) prepared at from approximately 5% to approximately 15% concentrations (w/w). Films/disks may be air or vacuumed dried and crosslinked by immersing them into $CaCl_2$ solutions. In certain embodiments, the NaCS hydrogel films will be crosslinked using $CaCl_2$ solutions that range in concentration from approximately 0.5% (w/w) to saturation.

In any of the hydrogel or scaffold embodiments taught or described herein, the hydrogel or scaffold further comprises an additional component such as, e.g., a cell, a growth factor, a proteoglycan, an additional polysaccharide, an excipient, carrier or adjuvant or combinations thereof.

In certain circumstances, ionic-complexing may not form a stable hydrogel long-term. Thus, in another embodiment, the functional structure of the soluble cellulose material, e.g., NaCS, can be preserved and unaltered by entrapping it in a hydrogel network formed by a non-functional soluble polysaccharide. Therefore, in another embodiment, a soluble cellulose material, e.g., NaCS, may be co-dissolve with a non-functional soluble polysaccharide, e.g., dextran, forming a mixture that can be selectively cross-linked by chemical means. Since NaCS is highly substituted, there are few sites available for cross-linking. Dextran, however, is a fully unsubstituted polysaccharide and can undergo facile crosslinking using chemical agents such as sodium trimetaphosphate (STMP) or diglycidyl ether compounds. (See Lack S, Dulong V, Picton L, Cerf D L, Condamine E. High-resolution nuclear magnetic resonance spectroscopy studies of polysaccharides crosslinked by sodium trimetaphosphate: a proposal for the reaction mechanism. *Carbohydrate Research* 2007; 342(7):943-53; See also Collins M N, Birkinshaw C. Comparison of the effectiveness of four different crosslinking agents with hyaluronic acid hydrogel films for tissue-culture applications. *Journal of Applied Polymer Science* 2007; 104(5):3183-91; See also Rogovina S Z, Akopova T A, Vikhoreva G A, Gorbacheva I N. Solid state production of cellulose-chitosan blends and their modification and the diglycidyl ether of oligo(ethylene oxide). *Polymer Degradation and Stability* 2001; 73(3):557-60). The result is a fully functional NaCS entrapped in a crosslinked dextran hydrogel.

In additional embodiments, the hydrogel or scaffold comprises an ionic cellulose compound and a complexing or chemical cross-linking agent. A wide variety of suitable chemical cross-linking agents are known in the art. For example, suitable cross-linking agents for use in the hydrogels described herein include those that react with, e.g., amines, sulfate groups, hydroxyl groups, glycosidic bonds, such as, e.g., polydiallyl dimethyl ammonium chloride (PDADMAC) and bisepoxides. (See, e.g., Crosslinking Of Polysaccharides: Methods And Applications; Pharmainfo.net, vol. 6 issue 2, 2008). In certain embodiments the cross-linking agent is a diglycidyl ether, e.g., diisosorbide bisepoxide. In certain embodiments, the amount of complexing or cross-linking agent included is from about 0.01% to about 20% (w/w) with respect to the weight of the hydrogel. In additional embodiments, the percent of complexing or cross-linking agent included is about 0.01, 0.1, 0.5, 1.0, 2.0, 3.0, 4.0, 5M, 6.0, 7.0, 8.0, 9.0, 10.0, 11.0, 12.0, 13.0, 14.0, 15.0, 16.0, 17.0, 18.0, 19.0, or 20.0% (w/w), and including all values in between.

In another aspect, a hydrogel or scaffold for use in tissue engineering or an implantable material is taught and described, the hydrogel or scaffold comprising at least two polysaccharides, such as, e.g., two water soluble cellulose compounds. In certain embodiments, the compounds are cross-linked as described herein, for example, by means of ionic interactions.

Seeding or loading of cells for in vitro and in vivo use, may be performed by any technique known to one skilled in the art. In one exemplary embodiment, NaCS powder is mixed with human MSCs in PBS and cross-linked using the optimized concentration of $CaCl_2$. In another exemplary embodiment, an NaCS gel is prepared and is vacuum loaded, using a previously reported technique (See Livingston T L, 2003; 85-A (10):1927-35), with. MSCs in PBS and then cross-linked using the optimized concentration of $CaCl_2$. In another exemplary embodiment, cross-linked NaCS gel will be vacuum loaded with MSCs. In one embodiment, the cell seeding density is about $2.5 \times 10^6$ cells/mL, which is based upon studies evaluating chondrogenesis in pellet cultures. (See Mackay A M, Beck S C, Murphy J M, Barry F P, Chichester C O, Pittenger M F. Chondrogenic differentiation of cultured human mesenchymal stem cells from marrow. *Tissue Engineering* 1998; 4(4):415-28). Metabolic activity and cell growth over time will be measured using the XTT kit according to the manufacturer's instructions (Biotium, USA).

Figure 7:
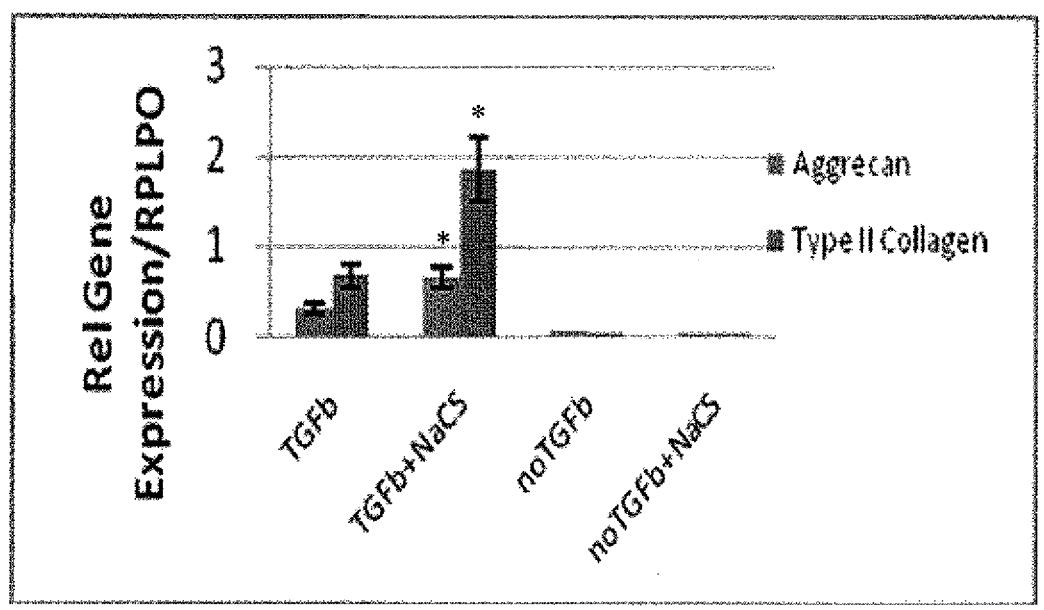
FIG. 7 shows relative gene expression for Type II collagen and aggrecan for human MSCs in chondrogenic media containing TGF-β (TGFb) alone or with NaCS (TGFb+NaCS). Controls were cultures without TGF-β (noTGFb) or without TGF-β but containing NaCS (noTGFb+NaCS). *$p<0.05$, statistically greater than TGFb.

In another aspect, taught and described herein are methods for preparing a hydrogel or scaffold to facilitate cell growth and differentiation or tissue regeneration and repair, e.g., cartilage repair, the method comprising the steps combining or admixing an aqueous solution and an effective amount of a water soluble cellulose compound, wherein the combination forms a hydrogel capable of acting as a support for the growth and/or differentiation of a cell, e.g., a progenitor or stem cell. In certain embodiments, the method further comprises a step of adding an effective amount of a polycation, a cation, a chemical cross-linker or a combination thereof, as taught and described herein. In additional embodiments, the method further comprises a step of adding an isolated, differentiable progenitor or stem cell, e.g., a MSC, wherein the cell grows and/or differentiates on the hydrogel or scaffold. In still another embodiment, the isolated, differentiable progenitor or stem cell differentiates on the hydrogel or scaffold into a chondrocyte and/or a cell displaying a chondrocyte-like phenotype. (See FIG. 7).

In certain embodiments, differentiation of MSCs in micromass pellet cultures or seeded onto hydrogels or scaffolds as taught and described, is assessed using biochemical, histochemical and molecular biology techniques known by those of skill in the art. Comparisons are made with articular chondrocytes. In certain embodiments, transcriptional factors and markers of early and late stage chondrocytes, hypertrophic chondrocytes and osteoblasts may be compared as an indicator of differentiation.

In certain exemplary embodiments, proliferation is evaluated at Days 7, 14, and 28 days in all hydrogel or scaffold groups and controls. Proliferation and metabolic activity is evaluated by DNA quantitation and MTT assay. For chondrogenesis, chondrogenic pellets formed from MSCs and chondrocytes and cell-laden scaffolds will be harvested at 7, 14, and 28 days and analyzed for glycosaminoglycan, Type II collagen, and proteoglycan synthesis. Glycosaminoglycan and proteoglycan synthesis is measured quantitatively using an ELISA kit (Blyscan™ Kit, Accurate Chemical and Scientific Corporation, Westbury, N.Y.). Highest levels in control pellets can be expected by day 14. (See Barry F, Boynton R E, Liu B, Murphy J M. Chondrogenic differentiation of mesenchymal stem cells from bone marrow: differentiation-dependent gene expression of matrix components. *Experimental Cell Research* 2001; 268:189-200). Type II collagen synthesis may be measured by an ELISA kit (Arthrogen-CIA, Chondrex, Inc.).

In additional embodiments, histological staining and confocal microscopy is performed of the pellets and cell-laden hydrogels or scaffolds at days 7, 14 and 28. For histology, the pellets are fixed in formalin 10%, dehydrated through graded alcohols, and embedded in paraffin. For example, sections are cut at a thickness of about 5 µm and stained with Alcian blue, Safranin-O, and Sirius Red. Alcian Blue stains both sulfated and carboxylated acid mucopolysaccharides and sulfated and carboxylated sialomucins. Safranin O in the orthochromatic form stains articular cartilage, mucin and mast cell granules on formalin-fixed, paraffin embedded tissue sections. Proteoglycans will stain red, cytoplasm will stain gray green and nuclei will stain black. Sirius Red dye can be used to differentiate different collagen types in tissue sections. Confocal microscopy may be utilized to visualize the cell interaction and overall morphology of the cells on the scaffolds using actin cystoskeleton stain (Alexa Fluor 488 phalloidin; Invitrogen, USA) and a nuclear stain ((4',6-diamidino-2-phenylindole, DAPI; Invitrogen, USA).

In certain other embodiments, real-time PCR and/or real-time reverse transcription (RT)-PCR is performed to assay for the gene expression of early markers of, e.g., fibromodulin and cartilage oligomeric matrix protein, mid-stage markers of aggrecan and versican, mature chondrocyte markers for type II collagen and chondroadherin, and sox9, a transcription factor, at, e.g., days 1, 14 and 28 days. In additional embodiments, optionally, additional factors are analyzed, including Sox-2, Oct-4 and NANOG as a marker for the undifferentiated MSC, as an indicator of stem cell self-renewal and maintenance. (See Greco S J, Liu K, Rameshwar P. Functional similarities among genes regulated by oct-4 in human mesenchymal and embryonic stem cells. *Stem Cells* 2007; 25(12): 3143-54). In additional embodiments, chondrocyte hypertrophic markers of Type X collagen, Type I collagen, matrix metalloproteinase 13, vascular endothelial growth factor (VEGF) and alkaline phosphatase will also be examined. (See Mueller). In additional embodiments, gene expression at day 0 for MSCs and chondrocytes is also examined. In any of the embodiments taught and described herein, quantitative RT-PCR analysis may be performed with the One Step QuantiTect SYBR Green RT-PCR Kit (Qiagen, CA, USA) using the MX4000 detection system (Stratagene, Calif., USA), according to the manufacturers' instructions.

Briefly, cells on scaffolds are harvested. Total RNA is isolated using the RNeasy Mini Kit (Qiagen) including the homogenization (QIA Shredder; Qiagen) and DNA digestion step (RNase Free DNase Set; Qiagen). The reverse transcription step will run for 30 min at 50° C., followed by PCR activation for 15 min at 95° C. Forty amplification cycles are run, consisting of 15 s denaturation at 94° C., 30 s of annealing at 55° C., and 30 s of extension at 72° C. For each reaction, a melting curve analysis of the RT-PCR product can be included. Samples are assayed in triplicate and the values are normalized to the relative amounts of the housekeeping gene RPLPO (ribosomal protein, large, PO) according to Muller et al. (See Muller P Y, Janovjak H, Miserez A R, Dobbie Z.

Processing of gene expression data generated by quantitative real-time RT-PCR. Biotechniques 2002; 32(6):1372-4).

In certain other embodiments, protein level expression for Oct-4, Sox-2, and Nanog can be evaluated, e.g., using western analysis. (See Greco). Briefly, rabbit anti-Oct4, -SOX-2, -NANOG, and fluorescein isothiocyanate (FITC)-goat anti-rabbit are purchased from Abcam (Cambridge, M.A.). Nuclear proteins can be extracted with the Nxtract kit according to the manufacturer's specified guidelines (Sigma-Aldrich). Total protein is determined with a Bio-Rad (Hercules, Calif.) DC protein assay kit. Extracts (15 μg) are treated with protease inhibitor and analyzed using, e.g., a 4%-20% SDS-polyacrylamide gel electrophoresis precast gels (Bio-Rad). Proteins are transferred onto membranes (PerkinElmer Life and Analytical Sciences) and incubated overnight with primary antibodies. Detection is performed with HRP-conjugated IgG. Primary and secondary antibodies are used at dilutions of 1/1,000 and 1/2,000, respectively. Membranes are stripped with Restore Stripping Buffer (Pierce, Rockford, Ill.) for reprobing with other antibodies. Cytoplasmic contamination of nuclear extracts is determined by reprobing the membranes with anti-ribosomal protein L28.

In certain additional embodiments, MSCs seeded onto hydrogels or scaffolds, or pellet cultures using MSCs and chondrocytes are cultured in either standard growth media (control), CCM+ or CCM−. Chondrocytes are cultured in CCM+ only. In certain embodiments, quantitative assays are performed on days 7, 14, and 28 or days 1, 14 and 28 days for gene expression. A sample size, n of 4, is generally used for all quantitative biochemical assays (glycosaminoglycan, Type II collagen, and proteoglycan) and histological analyses. A sample size, n of 9, is generally used for gene expression, since the studies are usually performed in a 96-well plate format. One way and two way ANOVAs can be performed to test for statistical differences between groups at each time point and over time, respectively for $p<0.05$. The Tukey-Kramer Method, $p<0.05$, is used to perform multiple comparisons between groups.

In another aspect, methods of treating and/or repairing a tissue, e.g., cartilage tissue, in a subject are taught and described, the method comprising administering to a subject an effective amount of a hydrogel or scaffold as taught and described herein in a pharmaceutically acceptable form, wherein the hydrogel or scaffold is effective for supporting, promoting, and/or enhancing the growth, regeneration, and/or repair of the tissue.

In another aspect, methods of treating arthritis are taught and described, the method comprising administering to a subject an effective amount of a hydrogel or scaffold as described herein in a pharmaceutically acceptable form, wherein the hydrogel or scaffold is effective for alleviating or ameliorating the symptoms of arthritis in the subject.

In certain embodiments, the methods as taught and described herein comprise administering the hydrogel or scaffold as taught and described herein, in combination with a pharmaceutically acceptable excipient, carrier or adjuvant. In additional embodiments, the methods further comprises a step of seeding a progenitor or stem cell, e.g., MSC, onto the hydrogel at a time prior to, subsequent to, contemporaneously or a combination thereof, of administering the hydrogel to the subject.

Applications and alternative embodiments include, but are not limited to, an injectible gel for filling cartilage defects, for cartilage repair, joint repair, and arthritis relief. The compositions of the present invention may also be combined with a fibrous scaffold for treating large defects. As described herein, the embodiments of the present invention useful to support and promote tissue and cartilage repair with or without the use of stem cells.

It was also surprisingly and unexpectedly discovered that the administration of an ionic, water soluble polysaccharide, e.g., NaCS, to cell culture media comprising a progenitor or stem cell, e.g., MSC, facilitates and/or enhances cell growth and/or differentiation. Accordingly, in another aspect, a cell culture media is taught and described, the cell culture media comprising an aqueous pH buffer and an effective amount of an ionic, water soluble polysaccharide. In certain embodiments, the water soluble polysaccharide is an anionic, water soluble cellulose compound. In another embodiment, the cell culture media comprises from about 0.01% to about 15% (w/w) of an anionic water soluble cellulose compound. In another embodiment, the cell culture media comprises from about 0.01% to about 0.5% (w/w) of an anionic water soluble cellulose compound. In additional embodiments, the anionic, water soluble cellulose compound is at least one of NaCS, NaCP or both. In yet another embodiment, the cell culture media further comprises an effective amount of a growth factor, proteoglycan, or polysaccharide.

In certain embodiments, the ability of NaCS in immobilizing growth factors similar to other sulfated glycosaminoglycans is utilized. (See Ishihara M, Sato M, Hattori H, Saito Y, Yura H, Ono K, et al. Heparin-carrying polystyrene (HCPS)-bound collagen substratum to immobilize heparin-binding growth factors and to enhance cellular growth. *J Biomed Mat Res* 2001; 56(4):536-44). Growth factors are naturally occurring substances capable of stimulating cellular growth, proliferation, repair and cellular differentiation. Usually, the growth factor is a protein or small molecule, e.g., a steroid hormone, which binds to specific receptors in/on the target cells. Growth factors are important for regulating a variety of cellular processes and typically act as signaling molecules between cells. Growth factors include, for example, bone morphogenic proteins, while fibroblast growth factors and vascular endothelial growth factors stimulate blood vessel differentiation (angiogenesis).

In another aspect, a method for culturing a progenitor or stem cell, e.g., MSC, is taught and described, the method comprising providing at least one isolated differentiable progenitor or stem cell, and culturing the cell in a cell culture media as taught and described herein. In certain embodiments the progenitor cell is an MSC, and the cell culture media promotes and/or enhances the growth and/or differentiation of the cell into a chondrocyte or a cell displaying a chondrocyte-like phenotype.

In any of the embodiments described herein, a therapeutic provided by the invention can be administered together with a pharmaceutically acceptable carrier, excipient, and/or an adjuvant. In additional embodiments, the invention provides therapeutic composition comprising a composition provided by the invention in combination with at least one additional biologically active and/or therapeutic agent such as an amino acid, peptide, polypeptide, chemical compound, drug, antibody or the like, or a combination thereof. For example, in an embodiment the hydrogel or scaffold composition comprises at least one additional biologically active and/or therapeutic agent such as an amino acid, peptide, polypeptide, chemical compound, drug, antibody or the like, or a combination thereof. The invention also provides methods of administering the same for the treatment or amelioration of a disease or disorder, including arthritis.

Specific examples of biologically beneficial ingredients that can be utilized in any of the embodiments described herein include: hyaluronic acid, growth factors (e.g. VEGF, TGF family), therapeutic antibodies (e.g., Humira), substance P, glucosamine, chondroitin sulphate, glycosaminoglycans, pain control agents (e.g morphine), synovial fluid and/or its components, steroids and derivatives. It should further be understood that the combinations which are to be included within this invention are those combinations useful for their intended purpose. The agents set forth below are illustrative for purposes and not intended to be limited. The combinations which are part of this invention can be the compositions provided by the present invention and at least one additional agent selected from the lists below. The combination can also include more than one additional agent, e.g., two or three additional agents if the combination is such that the formed composition can perform its intended function.

A non-exclusive list of exemplary growth factors that can be used in any of the embodiments taught and described herein include: Autocrine motility factor, Bone morphogenetic proteins (BMPs), Epidermal growth factor (EGF), Erythropoietin (EPO), Fibroblast growth factor (FGF), Granulocyte-colony stimulating factor (G-CSF), Granulocyte-macrophage colony stimulating factor (GM-CSF), Growth differentiation factor-9 (GDF9), Hepatocyte growth factor (HGF), Hepatoma derived growth factor (HDGF) Insulin-like growth factor (IGF), migration-stimulating factor, Myostatin (GDF-8), Nerve growth factor (NGF), brain-derived neurotrophic factor (BDNF) and other neurotrophins, Platelet-derived growth factor (PDGF), Thrombopoietin (TPO), Transforming growth factor alpha (TGF-α), Transforming growth factor beta (TGF-β), Vascular endothelial growth factor (VEGF), placental growth factor (PlGF), and/or Foetal Bovine Somatotrophin (FBS).

In one embodiment, TGF-β3 may be included in the hydrogel or scaffold matrix. TGF-β3 is detected during chondrogenesis during development in vivo. Immobilization is detected based on previously reported protocols. (See Ishihara M.). Immobilization studies used for different embodiments are as follows: various concentrations of TGF-β3 in BSA-PBS are added to cross-linked NaCS films overnight at 4° C. Wells are washed with BSA-PBS and immunofluorescent staining is performed using mouse anti-human TGF-β3 (Abeam, Inc.) followed by secondary, anti-mouse IgG conjugated with FITC (BD Biosciences, Inc). Fluorescent intensity is then detected using a fluorescent plate reader (FLX800, Biotek, Inc.) and correlated with the amount.

In any aspect of the invention, the therapeutic composition of the invention can be in any pharmaceutically acceptable form and administered by any pharmaceutically acceptable route, for example, by direct administration to the site or systemically. The therapeutic composition can be administered as an oral dosage, either single daily dose or unitary dosage form, for the treatment of a disease or disorder, e.g., arthritis. Such pharmaceutically acceptable carriers and excipients and methods of administration will be readily apparent to those of skill in the art, and include compositions and methods as described in the USP-NF 2008 (United States Pharmacopeia/National Formulary), which is incorporated herein by reference in its entirety. In certain aspects, the invention provides pharmaceutically acceptable formulations of the compounds described. These formulations include salts of the above compounds, e.g., sodium salts.

A pharmacological composition or formulation refers to a composition or formulation in a form suitable for administration, e.g., systemic administration, into a cell or subject, preferably a human. By "systemic administration" is meant in vivo systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

For parenteral administration the active compounds will generally be formulated for injection via the intravenous, intraarthricular, intrathecal, intramuscular, sub-cutaneous, intra-lesional, or even intraperitoneal routes. Typically, such compositions can be prepared as injectibles, either as liquid solutions or suspensions; solid forms suitable for using to prepare solutions or suspensions upon the addition of a liquid prior to injection can also be prepared; and the preparations can also be emulsified.

Preparations for administration of the therapeutic of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population).

The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Pharmaceutical compositions suitable for injectable use include sterile aqueous solutions (where water soluble) or dispersions and sterile powders for the extemporaneous preparation of sterile injectable solutions or dispersion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. For intravenous administration, suitable carriers include physiological saline, bacteriostatic water, Cremophor™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

In one embodiment, the active compounds are prepared with carriers that will protect the compound against rapid elimination from the body, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The preceding general areas of utility are given by way of example only and are not intended to be limiting on the scope of the present disclosure and appended claims. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional objects and advantages are expressly included within the scope of the present invention.

EXAMPLES

Materials and methods useful for practicing the present invention may be further described in one or more of the following: U.S. Pat. Nos. 6,689,166; and 6,790,528; and U.S. Published Pat. App. Nos. 2004-0018226; 2006-0204539; 2009-0325296; 2009-0028921; and 2006-0128012, the disclosures of which are all incorporated herein by reference in their entirety for all purposes.

Investigation of Chondrogenic Differentiation of Human MSCs on NaCS In Vitro.

For use in several exemplary embodiments, bone marrow is processed according to previously published protocols. (See Bruder S P, Kurth A A, Shea M, Hayes W C, Jaiswal N, Kadiyala S. Bone Regeneration by Implantation of Purified, Culture-Expanded Human Mesenchymal Stem Cells. J Orthop Res 1998; 16:155-62). Briefly, marrow samples are fractionated by centrifugation over a density cushion and plated on tissue culture flasks in Dulbecco's Modified Eagle's Medium (DMEM) containing 10% fetal bovine serum and 1% antibiotic (standard growth media). Cultures will be maintained at 37° C., 5% $CO_2$. Colony formation is monitored for a 14-17 day period and then, cells are subcultured. Cells are examined for morphology and cell surface markers typical for undifferentiated MSCs. (See Pitenger). Cells expressing CD44 and the absence of CD45 and CD34 surface antigens are verified by fluorescence-activated-cell-sorter. Human, articular chondrocytes are obtained from Asterand, Inc. and cultured using known protocols.

In certain embodiments, MSCs are seeded onto scaffolds, or grown in standard pellet cultures (as a positive control). They are cultured in serum-free chondrogenic complete medium (CCM+) consisting of 1 mM sodium pyruvate (Sigma), 0.1 mM ascorbic acid-2-phosphate (Wako), $1 \times 10^{-7}$ M dexamethasone (Sigma), 1% ITS+ (Collaborative Biomedical Products), and 10 ng/mL recombinant human TGF-β3 (Oncogene Sciences) dissolved in DMEM-low glucose for chondrogenesis, CCM without TGF-β3 (CCM−) or standard growth media. Comparisons are made with articular chondrocytes grown in the same pellet culture conditions using CCM+media, as a positive control.

FIG. 2 shows the structure of a regular 6-substituted sodium cellulose sulfate (NaCS). NaCS can be synthesized to have up to three sulfate groups per glucose residue. NaCS is known to be biocompatible and have low immunogenecity. It is also biodegradable by hydrolysis into smaller polysaccharides or glucose units. NaCS is structurally similar to glycosaminoglycans such as the chondroitin sulfates, dermatan sulfate, keratin sulfate and heparin (See FIG. 1).

The principal structural elements of hyaline cartilage are collagen fibers embedded in a stiff hydrogel matrix consisting of water and proteoglycans. The proteoglycans comprises glycosaminoglycans, the majority of which, e.g. 80%-90%, are chondroitin 4- and 6-sulfates. Cellulose sulfate, a monosaccharide polymer of 6-sulfonated glucose, has structural similarity to chondroitin sulfate. Moreover, cellulose sulfate compounds can be synthesized on a commercial scale, and have an enormous advantage in cost and availability over other glycosaminoglycans. Thus, in any of the hydrogel embodiments described herein, sodium cellulose sulfate (NaCS) may be utilized as a scaffold material for use in cartilage tissue repair.

NaCS is structurally similar to glycosaminoglycans such as the chondroitin sulfates, dermatan sulfate, keratin sulfate and heparin. It has been observed that receptor binding of growth factors is regulated by the interactions with sulfated glycosaminoglycans. (See Forsten-Williams K, Chu C L, Fannon M, Buczek-Thomas J A, Nugent M A. Control of growth factor networks by heparan sulfate proteoglycans. Annals of Biomedical Engineering 2008; 36(12):2134-48). Thus, the present invention also relates to the use of NaCS either used alone or with a fibrous network to provide support for, direct or a combination of both, stem cell chondrogenesis.

Divalent Cation Stabilization of NaCS Hydrogel or Scaffold.

NaCS is a negatively charged polyion with more than one negative charge per glucose residue. This structure allows for NaCS to be crosslinked by means of ionic interactions. The advantages of ionic crosslinking are mild preparation conditions and simple procedures, however, any crosslinking technique and bond type may be used. (See Liu Z, Jiao Y, Wang Y, Zhou C, Zhang Z. Polysaccharides-based nanoparticles as drug delivery systems. Advanced Drug Delivery Reviews 2008; 60(15):1650-62). While any material known to one skilled in the art that enables ionic crosslinking may be used, bivalent cations are preferred. For example, calcium ion crosslinking of negatively charged polysaccharides can be utilized to produced nanoparticles for delivery systems. Specifically, Ca-crosslinked alginate nanoparticles have been effectively used to encapsulate protein encoding plasmids. (See You J O, Peng C A. Calcium-alginate nanoparticles formed by reverse microemulsion as gene carriers. Macromolecular Symposia 2004; 219(147):153).

Figure 4:
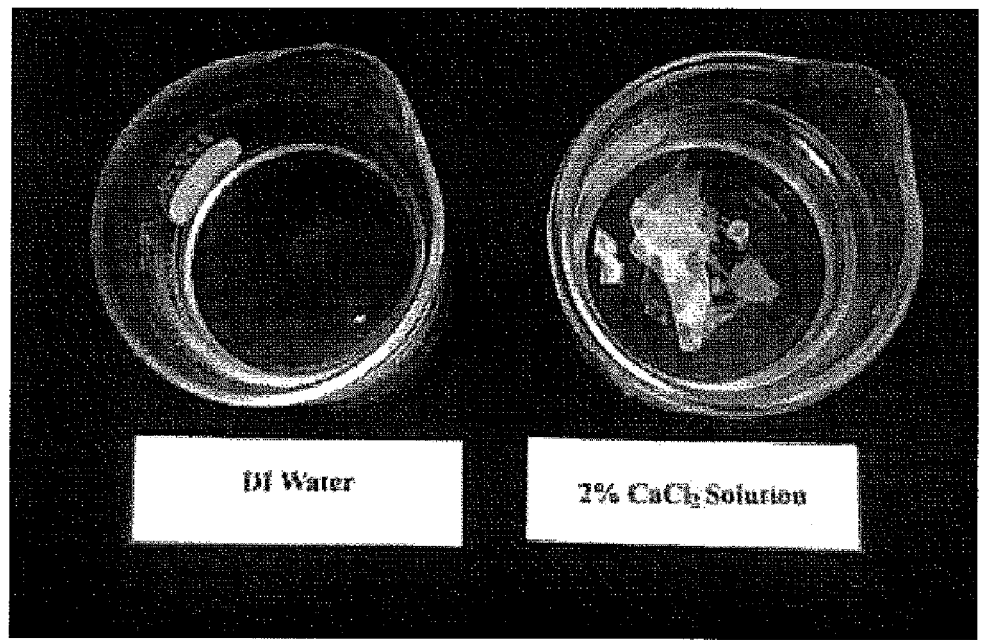
FIG. 4 shows images of 7% NaCS films immersed in DI water or DI water containing 2% $CaCl_2$. The white solid films in the $CaCl_2$ solution are insoluble, ionically crosslinked NaCS film. In DI water, the NaCS films dissolved.

To address the solubility in this example, NaCS was crosslinked to increase gel stability. Here, ionic crosslinking was performed using a bivalent (i.e., divalent) cation available in a water soluble salt, for example bivalent calcium (e.g. $CaCl_2$). In FIG. 4, films of 7% NaCS in DI water, cast, air dried, and immersed in solutions of DI water or DI water containing 2% $CaCl_2$ are shown. The white solid in the $CaCl_2$ solution is the insoluble, conically crosslinked NaCS film. Nothing is visible in the DI water, because in the absence of the $CaCl_2$, the NaCS film dissolved. Therefore, in an additional embodiment, the invention provides a scaffold comprising a soluble cellulose material, for example, NaCS, cross-linked by a bivalent cation, e.g., $Ca^{2+}$, $Ba^{2+}$, $Mg^{2+}$, $Fe^{2+}$, $Cu^{2+}$. In a preferred embodiment, the bivalent cation is calcium.

The range of $CaCl_2$ in DI water for these procedures is 0.5 to 5 wt %. Effective crosslinking was achieved using $CaCl_2$ concentrations of 2% or greater. Because each Ca2+ cation can complex with two sulfate groups on the sodium cellulose sulfate, the extent of complexation, which is related to the degree of crosslinking is expected to be high.

Figure 5:
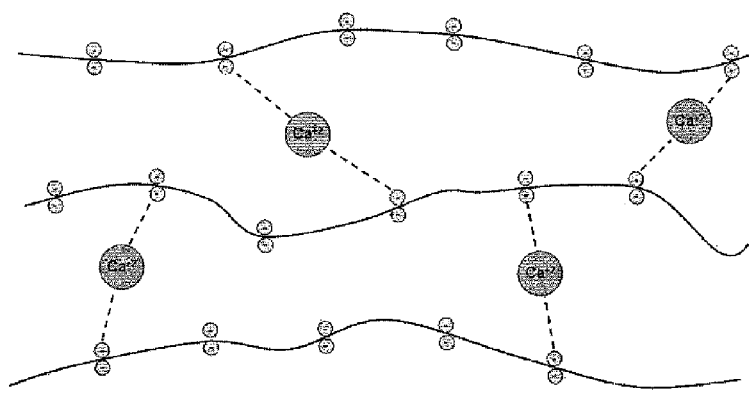
FIG. 5 shows a diagram of the mechanism for cross-linking NaCS

The characterization of NaCS hydrogels and gel-fiber constructs have been performed. FIG. 5 shows a representation of the mechanism of crosslinking NaCS with bivalent calcium. It is important to note that crosslinking can be achieved without complexing all the available sulfate groups. A crosslinking process involving all available sulfates groups would be so extensive that the material would become brittle and be unable to absorb water. There are indications that the Ca-crosslinked NaCS remains a flexible hydrogel suggesting that functional sulfates groups remain available. Other ionic cross-linking agents could be used such as $MgCl_2$. In certain embodiment, the hydrogel comprises soluble cellulose, e.g., NaCS, fiber matrix in which one or more fibers are cross-linked by a bivalent cation.

Chemical Crosslinking/Stabilization of NaCS Hydrogel.

Chemical crosslinking of exemplary embodiments of the present invention was also investigated. NaCS has hydroxyl groups that provide reactive sites for crosslinking (FIG. 2). In exemplary embodiments, NaCS was chemically crosslinked by using diglycidyl ethers, which are used extensively as cross-linking and chain extending reagents in polymers to increase molecular weight and to produce 3-dimensional networks. (Rogovina S Z, Akopova T A, Vikhoreva G A, Gorbacheva I N. Solid state production of cellulose-chitosan blends and their modification and the diglycidyl ether of oligo(ethylene oxide). *Polymer Degradation and Stability* 2001; 73:557-560). It was observed that isosorbide diglycidyl ether, a derivative of isosorbide which is in turn made from glucose, will react with the hydroxyl groups of complex carbohydrates to produce cross-linked 3-dimensional structures. Both the isosorbide unit and the glycerol units, which are the natural degradation products, are very hydrophilic. Crosslinking can be performed at room temperature, but in alkaline conditions which potentially limits embodiments of the present invention utilizing this technique for preparation in situ.

Constructs formed by coacervation (i.e., complexing) with or without chemical crosslinking are embraced by the present invention. It is important to note that coacervation can be achieved without complexing all the available sulfate groups. If all available sulfates groups were complexed, the material would become brittle and be unable to absorb water. It seems that the polyion complexed NaCS remains a flexible hydrogel suggesting that functional sulfates groups remain available.

Hydrogel with Fibrous Matrix.

Incorporation of water soluble cellulose compounds, in particular NaCS, into a scaffold construct either alone or in combination with a fibrous network may require the manipulation of the physical behavior of this material. For Example, in one embodiment, NaCS is cross-linked to form a more stable gel. In one embodiment, ionic crosslinking is used to crosslink NaCS to form the more stable gel.

NaCS is a long chain macromolecule of repeating glucose units that can be substituted to varying extents with anionic sulfate groups and made charge neutral with sodium cations. Since it is similar to sulfated glycosaminoglycans, NaCS could impart bioactivity that changes in nature with the level of sulfation. The polyanionic nature of NaCS is exploited in certain exemplary embodiments of the present invention by incorporating a novel design of self-assembled fibers within the gel using polyion coacervation. The fibers, which are insoluble in water, can provide additional mechanical support to the gel as well as potential adhesion properties to the surrounding tissue due to its cationic properties.

Embodiments of the present invention demonstrate that human MSCs on fibrous meshes grow and express enhanced levels of mature chondrocytic markers and a reduction in Sox2 expression, which is characteristic for an undifferentiated MSC. Without being bound by any particular theory, the inventors postulate that NaCS has structural similarities to natural GAGs, which imparts functional qualities that are similar to the functions of the natural GAGs when NaCS is used either alone or with a fibrous network support.

In order to more closely mimic a hydrogel-fibrous matrix, a stable, self-assembled web of fibers within the NaCS gel (FIG. 6*a*) was formed. NaCS is a polyanion and it can form a coacervate or polyion complex with a polycation, such as chitosan. In exemplary embodiments of the present invention NaCS gel modified to contain fibers that self-assemble using a simple method of forming a coacervate. This will provide additional mechanical support to the gel and this gel-fibrous construct has the potential of being formed in situ.

Figure 3:
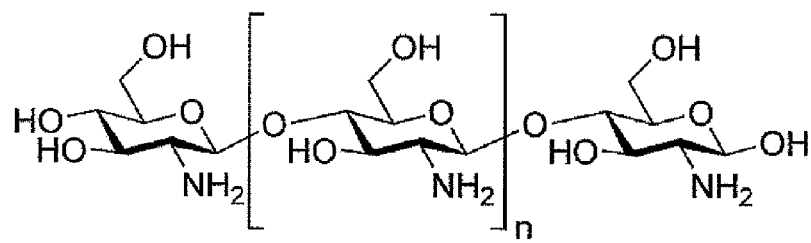
FIG. 3 shows an exemplary structure of (a) chitosan, (b) D-glucosamine, and (c) N-acetyl-D-glucosamine.
Figure 3:
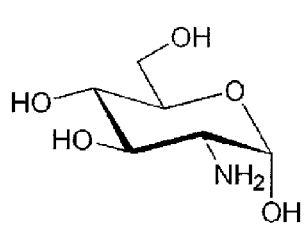
Figure 3:
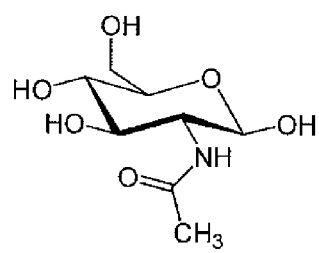

Chitosan (FIG. 3*a*) is a linear polysaccharide composed of randomly distributed β-(1-4)-linked D-glucosamine (deacetylated unit) (FIG. 3*b*) and N-acetyl-D-glucosamine (acetylated unit) (FIG. 3*c*). Chitosan is produced commercially by deacetylation of chitin, which is the structural element in the exoskeleton of crustaceans (crabs, shrimp, etc.) and cell walls of fungi. The degree of deacetylation (% DD) can be determined by NMR spectroscopy, and the % DD in commercial chitosans is in the range 60-100%. A common method for the synthesis of chitosan is the deacetylation of chitin using sodium hydroxide in excess as a reagent and water as a solvent. This reaction pathway, when allowed to go to completion (complete deacetylation) yields up to 98% product. The amino group in chitosan has a pKa value of ~6.5, which leads to a protonation in acidic to neutral solution with a charge density dependent on pH and the % DA-value. This makes chitosan water soluble and a bioadhesive which readily binds to negatively charged surfaces such as mucosal membranes. Chitosan enhances the transport of polar drugs across epithelial surfaces, and is biocompatible and biodegradable. Purified qualities of chitosans are available for biomedical applications.

The self-assembled fibers of various embodiments sulfated to different degrees were then given an injection of 1 to 10% concentrations (w/w) of chitosan (190,000-310,000 MW, Sigma-Aldrich) dissolved in dilute acetic acid (pH of 5.5) into the NaCS solution, which varied from 1 to 10% concentrations (w/w) in DI water and level of sulfation. The pH of chitosan was chosen for certain exemplary embodiments of the present invention because chitosan is soluble in dilute acidic solutions below pH of 6, where the amines become protonated and positively charged. (Pillai C K S, Paul W, Sharma C. Chitin and chitosan polymers: chemistry, solubility and fiber formation. *Progress in Polymer Science* 2009; 34:641-678). This pH also allows coacervation in the bulk NaCS without significantly altering the pH in the bulk of the gel.

Figure 6:
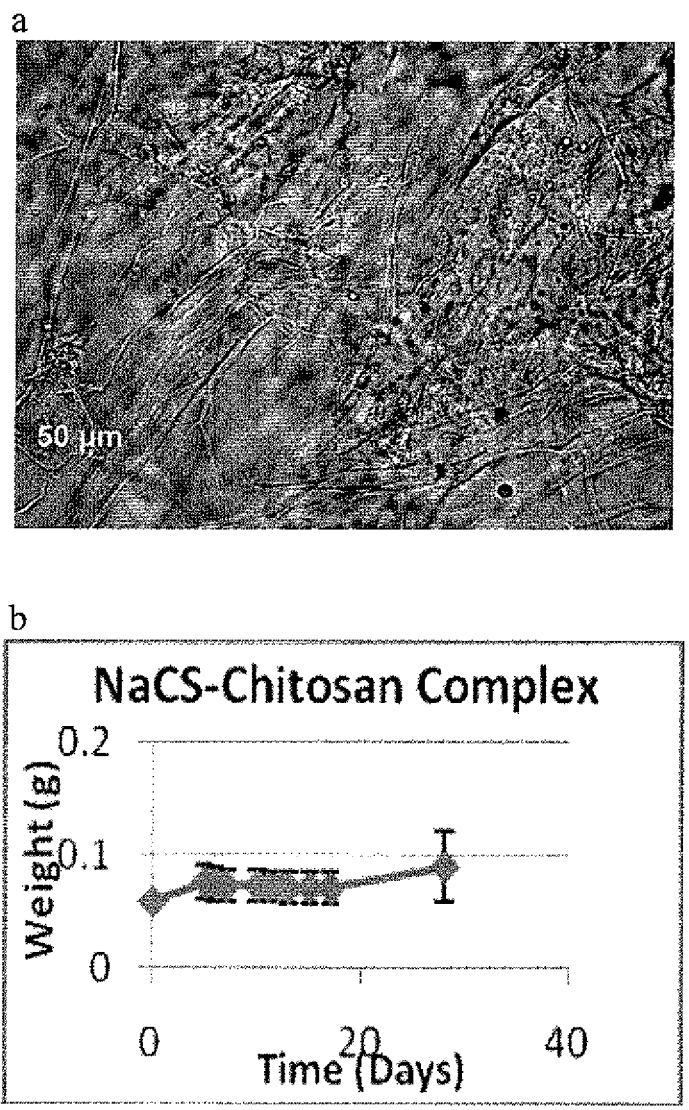
FIG. 6 shows (a) 1% chitosan solution is added to 1% NaCS gel and forms a web of microfilaments within the gel. Light micrograph, after 28 days in water, (b) Weight (g) of NaCS-chitosan complex (dried) after immersion in water for up to 28 days. Weight increase indicates that the water is retained over time.

By injecting a solution of chitosan into the NaCS gel, chitosan self-assembles into complexes with NaCS and forms fibers/filaments. This filamentous material is stable in water. Dry weight measurements for up to 28 days indicate that this coacervate is able to retain 1.5 to 2% water (FIG. 6b). In one embodiment of the present invention, chitosan was chosen as a possible polycation because it is a natural aminopolysaccharide with proven biocompatibility and biodegradability. (Pillai C K S, Paul W, Sharma C. Chitin and chitosan polymers: chemistry, solubility and fiber formation. *Progress in Polymer Science* 2009; 34:641-678). Also in its cationic form, chitosan has cartilage adhesive properties due to the electrostatic interactions with anionic glycosaminoglycans, proteoglycans and other negatively charged molecules. (DiMartino A, Sittinger M, Risbud M V. Chitosan: a versatile biopolymer for orthopaedic tissue-engineering. *Biomaterials* 2005; 26:5983-5990). Another advantage is this simple method of preparing self-assembled filaments within the gel, which could occur in situ. This fibrous construct provides additional mechanical integrity to the gel, provides an additional substrate for cell adhesion and also promotes scaffold adhesion with the surrounding cartilage tissue.

In an exemplary embodiment, self-assembled fibers were formed inside of 96-well non-adherent, polypropylene culture plates and then, MSCs either suspended in NaCS solution or in standard culture media were injected onto the fibers. Media containing $CaCl_2$ was added for polyion complexing of NaCS. The cells are seeded on top of the gel after neutralization. The exemplary constructs are cultured in serum-free chondrogenic complete medium (CCM+) consisting of 1 mM sodium pyruvate (Sigma), 0.1 mM ascorbic acid-2-phosphate (Wako), $10^{-7}$M dexamethasone (Sigma), 1% ITS+ (Collaborative Biomedical Products), and 10 ng/mL recombinant human TGF-β3 (Oncogene Sciences) dissolved in DMEM-high glucose for chondrogenesis, CCM without TGF-β3 (CCM−) or standard growth media. Proliferation and metabolic activity were evaluated at days 7, 14, and 28 days by DNA quantitation and MTT assay. Type II collagen synthesis ELISA kit (Arthrogen-CIA, Chondrex, Inc.) were determined at 7, 14, and 28 days.

Hydrogel Support of Chondrogenesis.

Current surgical procedures for the repair of cartilage tissue result in poor integration with surrounding hyaline cartilage and the formation of fibrocartilage instead of normal hyaline cartilage. The presence of fibrocartilage suggests that there is deficient bioactivity to promote the chondrocyte phenotype and/or a lack of supportive mechanical integrity. The goal of certain exemplary embodiments of the present invention, consequently, is providing cells capable of chondrogenesis to the defect site and to promote their differentiation using a novel scaffold that more closely mimics the cartilage ECM in both structure and function. Glycosaminoglycans have been shown to have bioactive properties due to their level and spatial distribution of sulfate groups. NaCS, which is a semi-synthetic derivative of cellulose, has largely been unstudied as a scaffold material for cartilage repair and can be tailored with varying sulfation to improve bioactive properties.

Bioactivity of NaCS, similar to other sulfated glycosaminoglycans (Ishihara M, Sato M, Hattori H, Saito Y, Yura H, Ono K, Masuoka K, Kikuchi M, Fujikawa K, Kurita A. Heparin-carrying polystyrene (HCPS)-bound collagen substratum to immobilize heparin-binding growth factors and to enhance cellular growth. *J Biomed Mat Res* 2001; 56:536-544), is shown by examining its level of interaction complexing with TGF-β3. This growth factor is routinely used in chondrogenic induction media for human MSCs and is detected during chondrogenesis during development in vivo. (Mackay A M, Beck S C, Murphy J M, Barry F P, Chichester C O, Pittenger M F. Chrondrogenic differentiation of cultured human mesenchymal stem cells from marrow. *Tissue Engineering* 1998; 4:415-428). TGF-β3 was detected using previously reported protocols (Ishihara M, Sato M, Hattori H, Saito Y, Yura. H, One K, Masuoka K, Kikuchi M, Fujikawa K, Kurita A. Heparin-carrying polystyrene (HCPS)-bound collagen substratum to immobilize heparin-binding growth factors and to enhance cellular growth. *J Biomed Mat Res* 2001; 56:536-544) using immunofluorescent staining and quantitation by a fluorescent plate reader.

Figure 8:
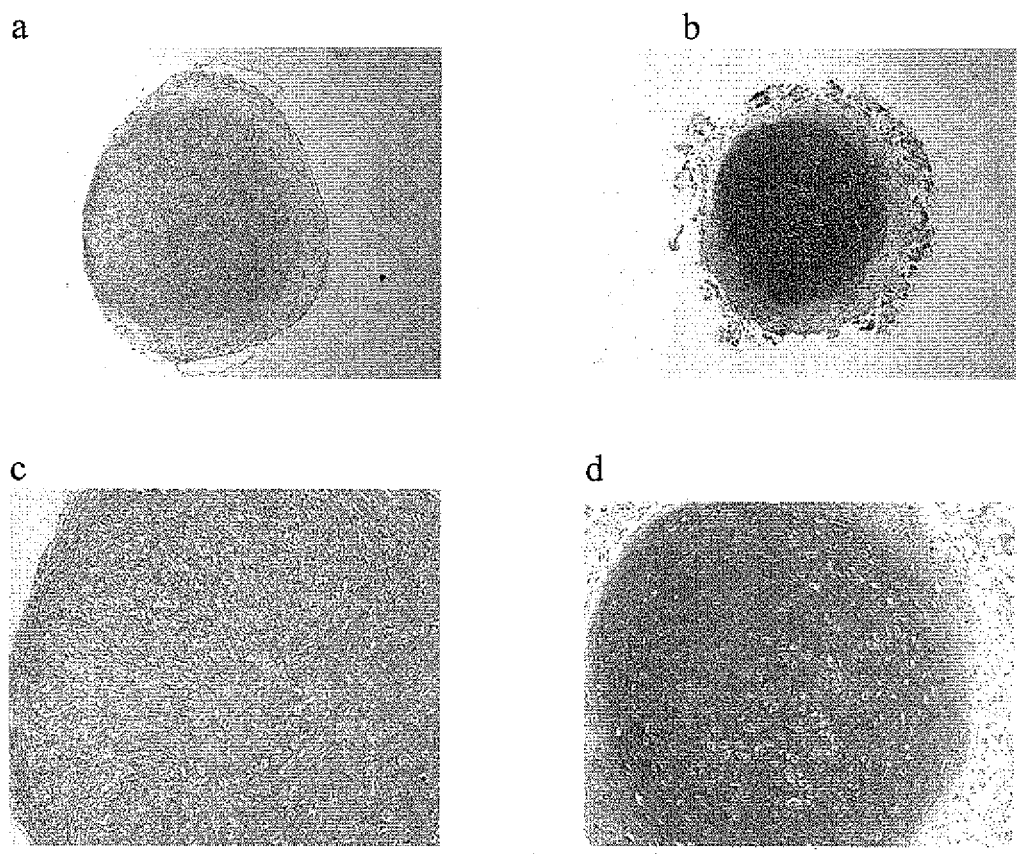
FIG. 8 shows histological micrographs of pellet cultures in chondrogenic differentiation media (with TGF-β3) a&c) without NaCS and b&d) with NaCS, (Safranin-O stains for proteoglycan where the intensity of the stain is directly proportional to the amount of proteoglycan (Camplejohn K L, Allard S A. Limitations of safranin-O staining in proteoglycan depleted cartilage demonstrated with monoclonal antibodies. Histochemistry 1988; 89:185-188), 4× and 10×obj., respectively. The control pellet with NaCS, but without TGF-β3, did not stain so NaCS does not contribute to the intense proteoglycan staining shown here.

Results indicate that human MSCs undergoing chondrogenic differentiation with NaCS (18-20% sulfation, or ~three sulfate substitutions per glucose residue) had higher gene expression for aggrecan and Type II collagen (FIG. 7), displayed a more uniform chondrocyte morphology and production of cartilage matrix histologically (FIG. 8) as compared to standard pellet cultures. Thus, certain embodiments of the present invention involve a novel scaffold to direct chondrogenesis for the use of this combination therapy in the repair of cartilage tissue defects in vivo.

Cartilage Explant.

The neocartilage formation and in vivo integration of a hydrogel or scaffold construct as taught and described herein with the surrounding cartilage tissue is examined. For certain exemplary embodiments, gel-fiber constructs with or without MSCs are inserted into cartilage explants and evaluated at 4 and 6 weeks in culture, as previously described. (Vinardell T, Thorpe S D, Buckley C T, Kelly D J. Chondrogenesis and integration of mesenchymal stem cells within an in vitro cartilage defect repair model. *Annals of Biomedical Engineering* 2009; 37:2556-2565). Standard cell culture environments can be used for explant cultures.

In one embodiment of the explant model, cartilage plugs of about 15 mm in diameter×2 mm thick are obtained from the femoropatellar joints of bovine forelegs (18-24 months of age), according to previously published protocols. (Rundell S A, Haut R C. Exposure to a standard culture medium alters the response of cartilage explants to injurious unconfined compression. *Journal of Biomechanics* 2006; 39:1933-1938). The forelegs come from the local abattoir within 3 hours of slaughter. Full-thickness cartilage cores are cut out to create an annulus and constructs are prepared in the center of the annulus (Vinardell T, Thorpe S D, Buckley C T, Kelly D J. Chondrogenesis and integration of mesenchymal stem cells within an in vitro cartilage defect repair model. *Annals of Biomedical Engineering* 2009; 37:2556-2565) in situ, depending upon the crosslinking/coacervation method used. Self-assembled fibers followed by calcium ion complexing are prepared in situ due to mild preparation conditions. Chemical crosslinking using isosorbide derivative is prepared and gel neutralized prior to inserting into the cartilage tissue. In one embodiment, $CaCl_2$ solution is added directly to the cut edge of the cartilage tissue prior to preparing the NaCS gel or gel-fiber construct in the defect in order to improve adhesion via ion complexing with the NaCS gel. MSCs are then analyzed for cell migration at the interface by immunofluorescent labeling with anti-human CD44 and co-labeling for anti-human Type II immunostaining to establish their differentiation. Explants are cultured in CCM+, CCM– or standard growth media.

The scaffolds of multiple embodiments of the present invention described herein enhance differentiation towards a mature chondrocyte phenotype. The explant cultures of certain exemplary embodiments of the present invention establish the feasibility of using these constructs in a cartilage defect as illustrated by their level of integration.

General Methods

Hydrogel or scaffold swelling. The swelling behavior and stability/degradation of the hydrogels is characterized by immersion of the gels in PBS or cell culture media at 37° C. for up to 3 months. The percent swelling will be given by % swelling=$((w_{hydrated}-w_{dry})/w_{dry})\times 100$, where $w_{hydrated}$ is the rehydrated gel and the $w_{dry}$ is the dried gel. The extent of swelling is then correlated to the crosslinker solution concentration. The overall stability/degradation of the hydrogel is evaluated over time by measuring changes in weight of the freeze-dried gel and molecular weight by GPC.

Histological staining, protein detection, and confocal microscopy. Histological staining and confocal microscopy is performed as previously described (Briggs T, Trieser M, Holmes P, Kohn J, Moghe P V, Livingston Arinzeh T. Osteogenic differentiation of human mesenchymal stem cells on poly(ethylene glycol)-variant biomaterials. *Journal of Biomedical Materials Research Part A* 2008; Epub ahead of print) are performed for the pellets and cell-laden scaffolds at days 7, 14 and 28. Types I and II collagen are observed by routine immunohistochemistry. Confocal microscopy is used to visualize the cell interaction and morphology on the scaffolds.

Protein level expression for Oct-4, Sox-2, and Nanog will be evaluated using western analysis. (Greco S J, Liu K, Rameshwar P. Functional similarities among genes regulated by oct-4 in human mesenchymal and embryonic stem cells. *Stem Cells* 2007; 25:3143-3154). Based on differentiation studies, constructs that best support differentiation and matrix production are pursued in explants studies.

Gene expression analysis. Gene expression studies are used to analyze the stage of differentiation of the MSCs within the constructs of various exemplary embodiments of the present invention. Real-time RT-PCR is performed for the gene expression of early markers of fibromodulin and cartilage oligomeric matrix protein, mid-stage markers of aggrecan and versican, mature chondrocyte markers for type II collagen and chondroadherin, and sox9, a transcription factor, at days 1, 14 and 28 days. Additional factors analyzed are Sox-2, Oct-4 and NANOG as a marker for the undifferentiated MSC, as an indicator of stem cell self-renewal and maintenance. (Greco S J, Liu K, Rameshwar P. Functional similarities among genes regulated by oct-4 in human mesenchymal and embryonic stem cells. *Stem Cells* 2007; 25:3143-3154). Chondrocyte hypertrophic markers including Type X collagen, Type I collagen, and alkaline phosphatase are examined. (Mueller M B, Tuan R S. Functional characterization of hypertrophy in chondrogenesis of human mesenchymal stem cells. *Arthritis and Rheumatism* 2008; 58:1377-138). Gene expression at day 0 for MSCs will be examined. Quantitative RT-PCR analysis will be performed with the One Step QuantiTect SYBR Green RT-PCR Kit (Qiagen, CA, USA) using the MX4000 detection system (Stratagene), according to the manufacturers' instructions, as reported by the PI (Arinzeh T, Weber N, Jaffe M. Electrospun electroactive polymer for regenerative medicine applications. US Non-provisional Patent Application, published 2009. p 1-25; Weber N, Lee Y S, Shanmugasundaram S, Jaffe M, Livingston Arinzeh T. Characterization and in vitro cytocompatibility of piezoelectric electrospun scaffolds. *Acta Biomaterialia* 2010; in revision) and others. (Muller P Y, Janovjak H, Miserez A R, Dobbie Z. Processing of gene expression data generated by quantitative real-time RT-PCR. Biotechniques 2002; 32:1372-1374).

The embodiments and examples provided herein are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

What is claimed is:

1. A composite hydrogel composition for facilitating cell growth or differentiation in cartilage comprising from 1% to 10% by weight of a water soluble anionic cellulose, and from 1% to 10% by weight of a polycationic polysaccharide, wherein the anionic water soluble cellulose forms a hydrogel, and wherein the polycationic polysaccharide forms a self-assembled fiber or filament network on the cellulose hydrogel, wherein the composition mimics the natural extracellular matrix of cartilage; and a mesenchymal stem cell (MSC) contained in or on the hydrogel, wherein the composition facilitates cell growth or differentiation of the MSC, wherein the water soluble anionic cellulose is sodium cellulose sulfate having from about 18% to about 20% sulfation.

2. The composition of claim 1, wherein the sodium cellulose sulfate is sulfated on at least one position of the glucose unit selected from the group consisting of positions 2, 3, 6, and combinations thereof.

3. The composition of claim 2, wherein the composition further comprises a cellulose sulfate compound with from about 6% to about 12% sulfation, or a cellulose sulfate compound having from about 13% to about 17% sulfation or a combination thereof.

4. The composition of claim 2, wherein the sodium cellulose sulfate is sulfated at positions 2, 3 and 6 of the glucose unit.

5. The composition of claim 1, wherein the polycationic polysaccharide is chitosan.

6. The composition of claim 5, wherein the chitosan has a molecular weight of from about 190 kilodalton (kDa) to about 310 kDa.

7. The composition of claim 1, wherein the hydrogel retains from about 1.5% to about 2% by weight of water.

8. The composition of claim 5, wherein the chitosan fibers in the hydrogel form interfiber spacings of from 10 µm to about 1 mm.

9. The composition of claim 8, wherein the interfiber spacings are from 100 µm to about 1 mm.

10. The composition of claim 1, further comprising a cation, wherein the polymer network is complexed or stabilized by ionic interactions.

11. The composition of claim 10, wherein the cation is at least one of calcium, magnesium, iron(II), manganese(II) or a combination thereof.

12. The composition of claim 1, further comprising a chemical cross-linking agent.

13. The composition of claim 12, wherein the chemical cross-linking agent is a diglycidyl ether.

14. The composition of claim 13, wherein the diglycidyl ether is isosorbide diglycidyl ether.

15. The composition of claim 14, wherein the diglycidyl ether is diisosorbide bisepoxide.

16. The composition of claim 1, further comprising a pH buffer.

17. The composition of claim 1, comprising an MSC-derived, differentiated cell.

18. The composition of claim 17, wherein the MSC-derived, differentiated cell expresses aggregan or type II collagen or both.

19. The composition of claim 1, further comprising a growth factor.

20. The composition of claim 19, wherein the growth factor is transforming growth factor beta (TGF-β).

21. The composition of claim 1, wherein the hydrogel is pre-formed in vitro.

22. The composition of claim 1, wherein the hydrogel is formed in vivo or in situ.

23. The composition of claim 1, wherein the composition is adapted for injection in vivo and/or in situ in a subject, and wherein the injectable hydrogel is capable of facilitating cell growth or differentiation.

24. The composition of claim 1, wherein the fiber or filament is an electrospun fiber or filament.

25. A composite hydrogel composition for facilitating mesenchymal stem cell growth or differentiation comprising a polymer network comprising from about 1% to about 10% (w/w) of a sodium cellulose sulfate compound, from about 1% to about 10% (w/w) of chitosan, wherein the sodium cellulose sulfate has from about 18% to about 20% sulfation, and wherein the polymer network-fiber matrix forms a cell attachment surface that facilitates mesenchymal stem cell growth or differentiation.

26. A method of preparing the hydrogel composition of claim 25 comprising the steps of:
admixing an aqueous solution having from about 1% to about 10% (w/w) of a sodium cellulose sulfate compound, and from about 1% to about 10% (w/w) of chitosan, wherein the chitosan forms fiber or filament matrix, and wherein the sodium cellulose sulfate and chitosan forms a polyionic complex.

27. The method of claim 26, comprising the step of seeding an isolated differentiable human mesenchymal stem cell (hMSC) on the hydrogel composition.

28. The method of claim 27, comprising the step of growing the hMSCs so that the isolated differentiable hMSCs differentiate into a mature cell phenotype on the hydrogel.

29. A method of treating or repairing cartilage tissue in a subject in need of such repair, the method comprising administering to said subject an effective amount of a hydrogel composition according to claim 1.

30. A method of treating arthritis in a subject in need of such treatment, the method comprising administering to said subject an effective amount of a hydrogel according to claim 1.

* * * * *